United States Patent
Ohishi

(10) Patent No.: US 10,080,532 B2
(45) Date of Patent: Sep. 25, 2018

(54) X-RAY DIAGNOSTIC APPARATUS

(71) Applicant: Toshiba Medical Systems Corporation, Otawara-shi (JP)

(72) Inventor: Satoru Ohishi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/734,105

(22) Filed: Jun. 9, 2015

(65) Prior Publication Data

US 2015/0351712 A1    Dec. 10, 2015

(30) Foreign Application Priority Data

Jun. 10, 2014  (JP) ................. 2014-119926

(51) Int. Cl.
    *A61B 6/00* (2006.01)
    *A61B 6/03* (2006.01)
    *A61B 6/02* (2006.01)
    *A61B 6/10* (2006.01)

(52) U.S. Cl.
    CPC ............ *A61B 6/4014* (2013.01); *A61B 6/027* (2013.01); *A61B 6/032* (2013.01); *A61B 6/102* (2013.01); *A61B 6/4441* (2013.01); *A61B 6/485* (2013.01); *A61B 6/487* (2013.01); *A61B 6/504* (2013.01); *A61B 6/5205* (2013.01); *A61B 6/5294* (2013.01); *A61B 6/545* (2013.01)

(58) Field of Classification Search
    None
    See application file for complete search history.

(56) References Cited

U.S. PATENT DOCUMENTS

| | | | |
|---|---|---|---|
| 6,113,264 A * | 9/2000 | Watanabe | A61B 6/4441 378/196 |
| 8,538,505 B2 | 9/2013 | Brunner et al. | |
| 2004/0066906 A1* | 4/2004 | Hornegger | A61B 6/02 378/197 |
| 2005/0286679 A1* | 12/2005 | Sakaguchi | A61B 6/032 378/8 |
| 2007/0098132 A1* | 5/2007 | Conwell | A61B 6/032 378/4 |

(Continued)

FOREIGN PATENT DOCUMENTS

| | | |
|---|---|---|
| JP | 2006-110372 | 4/2006 |
| JP | 2010-220668 | 10/2010 |

OTHER PUBLICATIONS

"X-ray Diagnostic Apparatus", machine translation of JP2006110372 A. Retrieved from Proquest Dialog Sep. 23, 2016.*

*Primary Examiner* — Michael Logie
(74) *Attorney, Agent, or Firm* — Oblon, McClelland, Maier & Neustadt, L.L.P.

(57) ABSTRACT

According to one embodiment, an X-ray diagnostic apparatus comprises a first imaging system, a second imaging system, a first support member, a second support member, control circuitry, and a reconstruction circuitry. The first projection data corresponds to a first imaging angle range. The second projection data corresponds to a second imaging angle range. A deficiency angle as an angle at which no imaging is performed is provided between the first imaging angle range and the second imaging angle range to make an imaging angle range in the projection data group have discontinuity.

19 Claims, 10 Drawing Sheets

(56) References Cited

U.S. PATENT DOCUMENTS

| | | | |
|---|---|---|---|
| 2008/0019474 A1* | 1/2008 | Nakanishi | A61B 6/032 |
| | | | 378/9 |
| 2011/0044525 A1* | 2/2011 | Ohishi | A61B 6/4014 |
| | | | 382/132 |
| 2013/0028388 A1* | 1/2013 | Yoshida | A61B 6/4441 |
| | | | 378/190 |
| 2015/0238159 A1* | 8/2015 | Al Assad | A61B 6/5258 |
| | | | 378/5 |

* cited by examiner

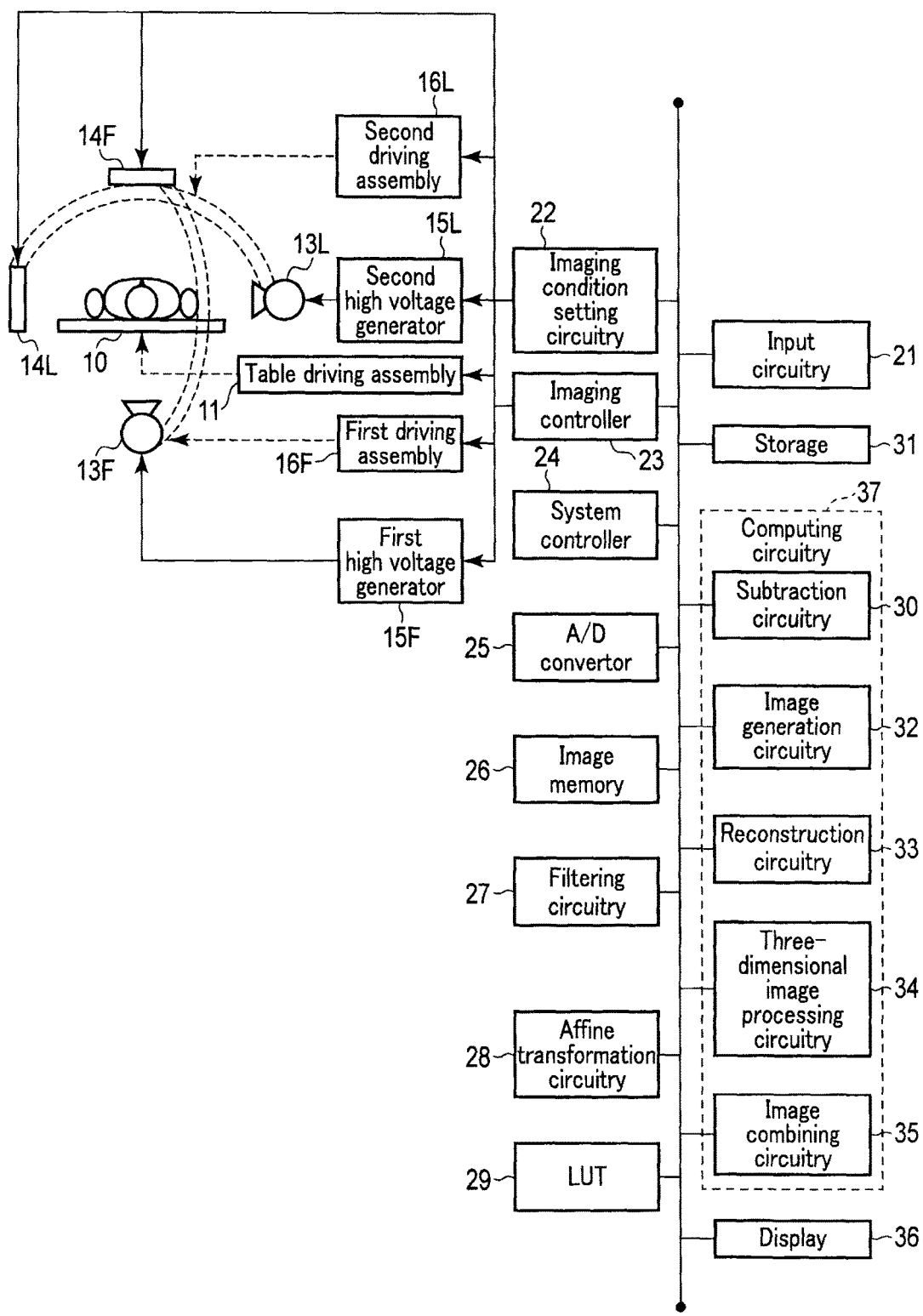
F I G. 1

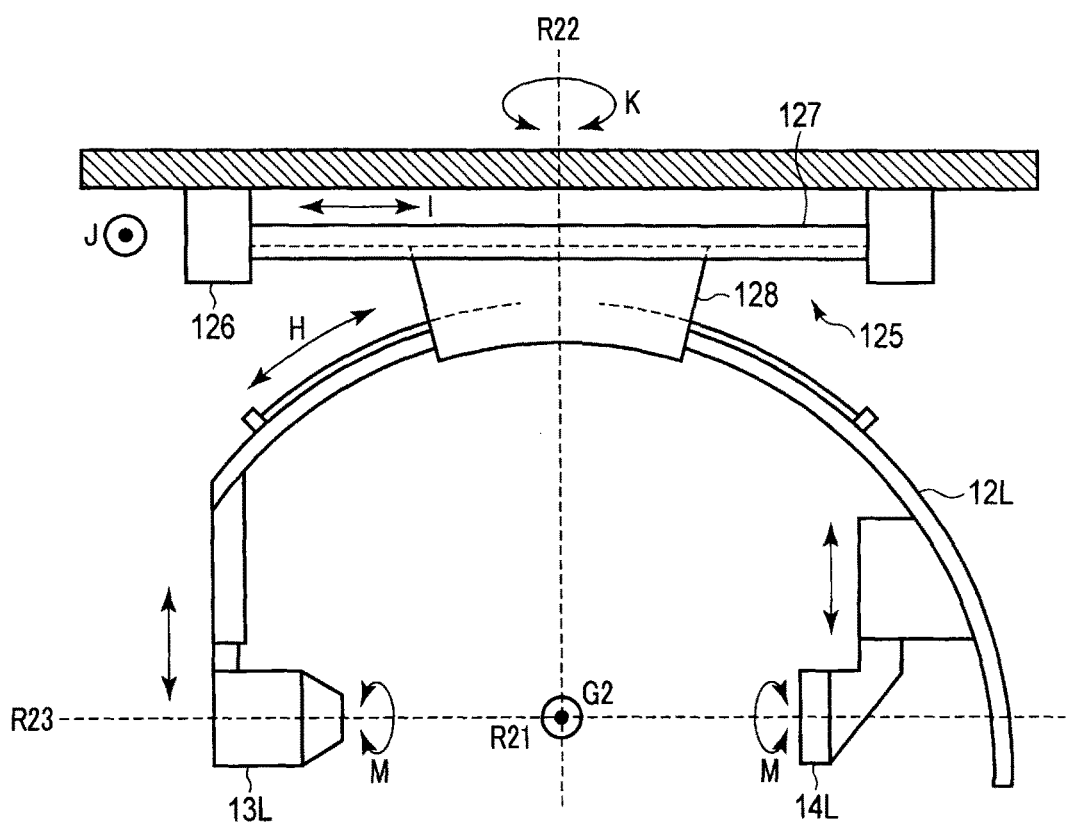
F I G. 3

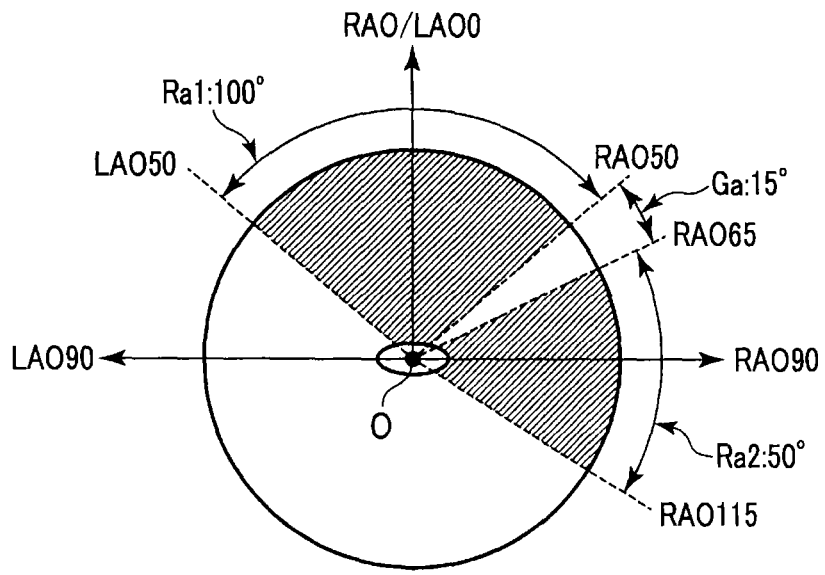
F I G. 8A
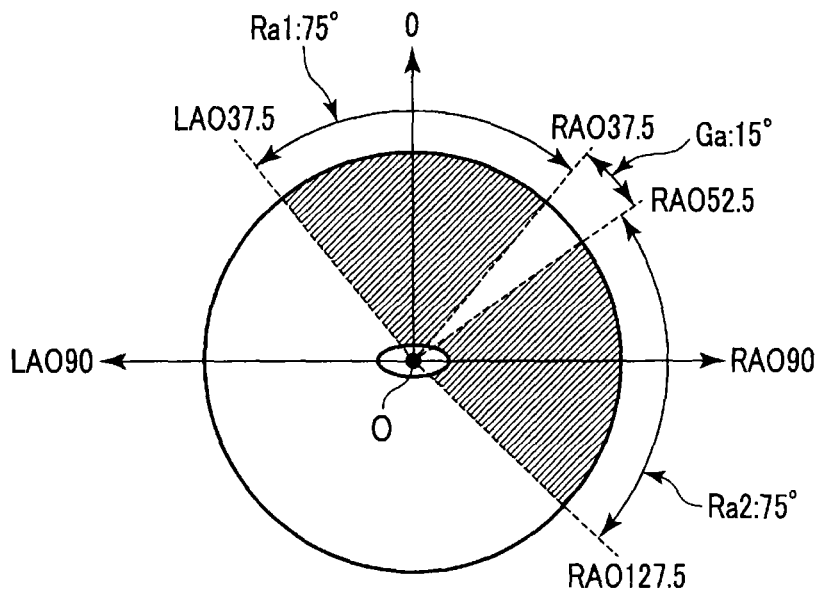
F I G. 8B

X-RAY DIAGNOSTIC APPARATUS

CROSS-REFERENCE TO RELATED APPLICATIONS

This application is based upon and claims the benefit of priority from the prior Japanese Patent Application No. 2014-119926, filed Jun. 10, 2014 the entire contents of which are incorporated herein by reference.

FIELD

Embodiments described herein relate generally to an X-ray diagnostic apparatus.

BACKGROUND

In intervention (intravascular treatment) or angiographic examination, the user inserts a catheter into a blood vessel from, for example, a region near the groin and advances the catheter to a desired position. The user performs the operation of advancing the catheter or a guidewire going forward through the catheter to a desired position under radiographic fluoroscopy. In general, no blood vessel can be seen on an X-ray fluoroscopic image. For this reason, the user grasps the position of the catheter or guidewire in the human structure by seeing an X-ray fluoroscopic image and operates the catheter or guidewire by using knowledge concerning a blood vessel structure at the position. If, however, a blood vessel structure is complicated and it is difficult to insert the catheter or guidewire, it is necessary to enhance the contrast of blood vessels with a contrast medium or the like under X-ray fluoroscopy. However, if injection of a contrast medium into a patient is continued, it may lead to renal dysfunction or the like.

For this reason, the user uses a road map in intervention or angiographic examination. Traditional 2D road mapping is a function of displaying, as a road map image, a DSA (Digital Subtraction Angiography) image obtained by subtracting object images before and after the injection of a contrast medium from each other while superimposing the image on a real-time X-ray fluoroscopic image. Although the DSA image is used in this case, it is possible to use other types of images as long as they can enhance the contrast of blood vessels. For example, it is possible to use an X-ray contrast image concerning an object after the injection of a contrast medium. It is also possible to use an image depicting blood vessel centerlines, an image with enhanced blood vessel walls, and the like which are obtained by processing a DSA image and an X-ray contrast image.

The 2D road mapping is a function of displaying a superimposed image obtained by positionally aligning a real-time fluoroscopic image with a 2D road map image. A 2D road map image is an image explicitly showing the running of blood vessels in a patient. For example, a 2D road map image is a DSA image or the like. A DSA image can be acquired routinely. For this reason, 2D road maps are often used in intervention and angiographic examination. However, it is difficult to grasp depth information concerning blood vessels from a DSA image. For this reason, the user changes the observation direction (imaging direction) of blood vessels. Every time the user changes the observation direction of blood vessels, it is necessary to obtain an additional DSA image corresponding to the observation direction after the change. If, therefore, the user frequently changes the observation direction of blood vessels, it requires many tasks, resulting in an increase in the dose of contrast medium injected into the patient.

A 3D road mapping is a function of displaying a 3D road map image and a real-time fluoroscopic image upon positionally aligning them with each other. A 3D road map image differs from a 2D road map image in that it is available to generate 3D road map images observed from any positions or any angles by 3D image processing. A 3D blood vessel image data is formed based on a plurality of DSA images having different imaging angles. A plurality of DSA images having different imaging angles are acquired while one imaging system is rotated through 200° or more around an object at high speed (this operation will be called rotational DSA imaging hereinafter). A 3D blood vessel image data has 3D blood vessel information. Therefore, in 3D road mapping, a 3D road map image is generated from 3D blood vessel image in accordance with (following) a change in observation direction. This allows the user to easily change the observation direction without re-injecting a contrast medium into a patient. In addition, if a 3D road map image is a rendering image, shading is applied to the image. This allows the user to discriminate the anteroposterior relationship (in the depth direction) between blood vessels to some extent.

As described above, 3D road mapping is a function useful from the viewpoint of three-dimensionally grasping a blood vessel structure. However, in order to form a 3D road map image, it is necessary to completely interrupt an operation when acquiring rotational DSA images to generate 3D blood vessel image data. In addition, it takes much time for the acquisition, and requires a further dose of both contrast medium and X-ray exposure. For such reasons, a 3D road map is not used for the purpose of the navigation of a catheter or guidewire in practice. However, previous 3D blood vessel image gives us highly accurate and detailed vessel structures. For navigation purpose, this is much more than necessary level. It should be sufficient to provide the branching angle of blood vessels at bifurcation area for inserting catheter or guidewire into interested branch. There has been proposed no 3D road map from such viewpoint.

BRIEF DESCRIPTION OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an X-ray diagnostic apparatus according to an embodiment;

FIG. 3 is a view showing an example of the outer appearance of the second imaging system (lateral system);

FIG. 8A is a view showing the first imaging angle range and the second imaging angle range set based on rotational speeds in the second example;

FIG. 8B is a view showing the first imaging angle range and the second imaging angle range which are set to increase the effect of suppressing the image quality deterioration of a 3D image in the second example;

DETAILED DESCRIPTION

Figure 2:
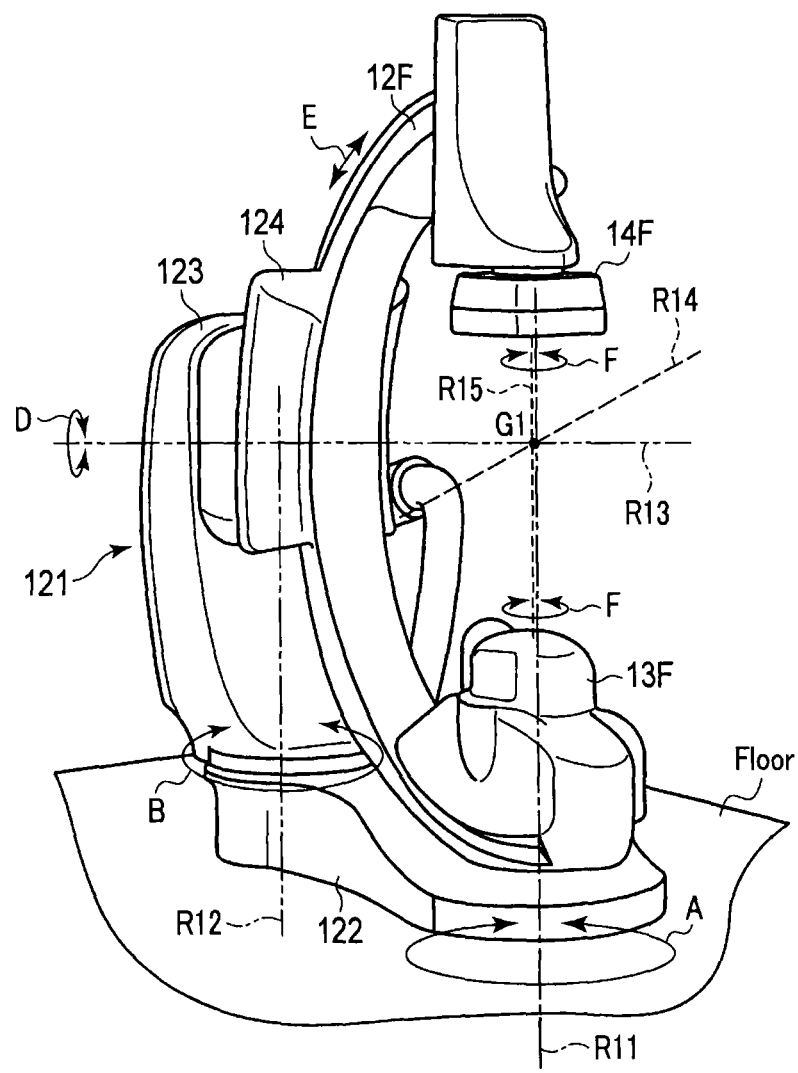
FIG. 2 is a perspective view showing an example of the outer appearance of the first imaging system (frontal system)

In general, according to one embodiment, an X-ray diagnostic apparatus comprises a first imaging system, a second imaging system, a first support member configured to support the first imaging system so as to allow the first imaging system to rotate about a first rotation axis, a second support member configured to support the second imaging system so as to allow the second imaging system to rotate about a second rotation axis parallel to the first rotation axis, control circuitry configured to control the first imaging system, the second imaging system, the first support member, and the second support member, and reconstruction circuitry configured to generate data of a reconstructed image by performing reconstruction based on a projection data group including a plurality of first projection data obtained with rotational imaging by the first imaging system and a plurality of second projection data obtained with rotational imaging by the second imaging system. The first projection data corresponds to a first imaging angle range. The second projection data corresponds to a second imaging angle range. A deficiency angle as an angle at which no imaging is performed is provided between the first imaging angle range and the second imaging angle range to make an imaging angle range in the projection data group have discontinuity.

An X-ray diagnostic apparatus according to this embodiment will be described below with reference to the accompanying drawing. Note that the same reference numerals in the following description denote constituent elements having almost the same functions and arrangements, and a repetitive description will be made only when required.

FIG. 1 is a block diagram showing the arrangement of an X-ray diagnostic apparatus according to this embodiment.

An X-ray diagnostic apparatus 1 according to this embodiment (to be referred to as the X-ray diagnostic apparatus 1 hereinafter) includes an imaging apparatus and a data processing apparatus. The imaging apparatus includes two imaging systems. The imaging apparatus is constituted by a first imaging system F as a frontal system (frontal: F), a second imaging system L as a lateral system (lateral: L), and a table apparatus.

The table apparatus includes a table 10 and a table driving assembly 11. The table 10 movably supports a top on which a patient lies. The top is moved by causing an imaging controller 23 to drive the table driving assembly 11.

The first imaging system F includes a C-arm 12F, a first X-ray generator 13F, a first X-ray detector 14F, first high voltage generator 15F, and a first driving assembly 16F. The C-arm 12F is a C-shaped holding apparatus. The C-arm 12F can be rotated and moved by driving the first driving assembly 16F under the control of the imaging control unit 23 (to be described later). The C-arm 12F holds the first X-ray generator 13F at its one end. The first X-ray generator 13F is constituted by the first X-ray tube (not shown) and the first collimator (not shown). The first X-ray tube generates X-rays from an X-ray focal point upon receiving a high voltage (tube voltage) and a tube current from the first high voltage generator 15F. The first collimator is attached to the radiation window of the first X-ray tube to adjust an X-ray irradiation field on the detection surface of the first X-ray detector 14F. It is possible to reduce unnecessary exposure of a patient by adjusting an X-ray irradiation field using the first collimator. The C-arm 12F holds the first X-ray detector 14F at its other end so as to make it face the first X-ray generator 13F. The first X-ray detector 14F includes a plurality of X-ray detection elements. The plurality of X-ray detection elements are arranged in a two-dimensional array. The two-dimensional array detector is called an FPD (Flat Panel Detector). Each element of the FPD detects light converted from the X-rays, emitted from the first X-ray generator 13F and transmitted through a patient. Each element of the FPD outputs an electrical signal corresponding to detected light intensity corresponds to X-ray intensity. Note that the first X-ray detector 14F may be formed from a combination (I.I-TV) of an image intensifier and a TV camera. A line connecting the focal point of the first X-ray tube to the center of the detection surface of the first X-ray detector 14F is defined as the first imaging axis.

FIG. 2 is a perspective view showing an example of the outer appearance of the first imaging system F.

The C-arm 12F is rotatably held by a C-arm holding apparatus 121. The C-arm holding apparatus 121 includes a floor swivel arm 122, a stand 123, and a C-arm holder 124. The floor swivel arm 122 is provided on the floor surface so as to be able to swivel (arrow A) on its one end about an almost vertical floor rotation axis R11. The stand 123 is supported on the other end of the floor swivel arm 122 so as to be able to axially rotate (arrow B) about a stand rotation axis R12 parallel to the floor rotation axis R11. The stand 123 supports the C-arm holder 124 so as to allow it to axially rotate (arrow D; holder rotation) about a C-arm horizontal rotation axis R13 orthogonal to the floor rotation axis R11 and the stand rotation axis R12 and almost parallel to the floor surface. The C-arm holder 124 supports the C-arm 12F so as to allow it to slidably rotate (arrow E) about a slide rotation axis R14 orthogonal to the floor rotation axis R11 and the C-arm horizontal rotation axis R13 and almost parallel to the floor surface. In addition, the first X-ray generator 13F and the first X-ray detector 14F can rotate (arrow F) around a first imaging axis R15. The first imaging axis R15 is defined by an axis connecting the X-ray focal point of the first X-ray tube to the central point of the detection surface of the first X-ray detector 14F. The rotation axis R11, the rotation axis R13, the rotation axis R14, and the rotation axis R15 intersect with each other at an isocenter (imaging fixed point) G1.

The second imaging system L includes an Ω-arm 12L, a second X-ray generator 13L, a second X-ray detector 14L, a second high voltage generator 15L, and a second driving assembly 16L. The Ω-arm 12L is a Ω-shaped holding apparatus. The Ω-arm 12L can be rotated and moved by driving the second driving assembly 16L under the control of the imaging controller 23 (to be described later). The Ω-arm 12L holds the second X-ray generator 13L at its one end. The Ω-arm 12L holds the second X-ray detector 14L at its other end so as to make it face the second X-ray generator 13L. A description of the second X-ray generator 13L is the same as that of the first X-ray generator 13F described above. In addition, a description of the second X-ray detector 14L is the same as that of the first X-ray detector 14F described above. A line connecting the focal point of the second X-ray tube to the center of the detection surface of the second X-ray detector 14L is defined as the second imaging axis.

FIG. 3 is a view showing an example of the outer appearance of the second imaging system L.

The Ω-arm 12L is rotatably held by an Ω-arm holding apparatus 125. The Ω-arm holding apparatus 125 includes traveling rails 126, a slider base 127, an Ω-arm holder 128. The Ω-arm 12L is suspended from the slider base 127 through the Ω-arm holder 128. The Ω-arm holder 128 supports the Ω-arm 12L so as to allow it to slidably rotate (arrow H) about a slide rotation axis R21. The slider base 127 is engaged so as to be movable in a direction (direction J; depth direction) along the traveling rails 126 laid on the ceiling surface and a direction between the traveling rails (a direction almost parallel to the ceiling surface and perpendicular to the direction along the traveling rails; arrow I). The slider base 127 supports the Ω-arm holder 128 so as to allow it to axially rotate (arrow K; holder rotation) about an almost vertical Ω-arm rotation axis R22. The second X-ray generator 13L and the second X-ray detector 14L can rotate (arrow M) about a second imaging axis R23. The second imaging axis R23 is defined by an axis connecting the X-ray focal point of the second X-ray tube to the central point of the detection surface of the second X-ray detector 14L. The rotation axis R21, the rotation axis R22, and the rotation axis R23 intersect with each other at an isocenter (imaging fixed point) G2.

Figure 4:
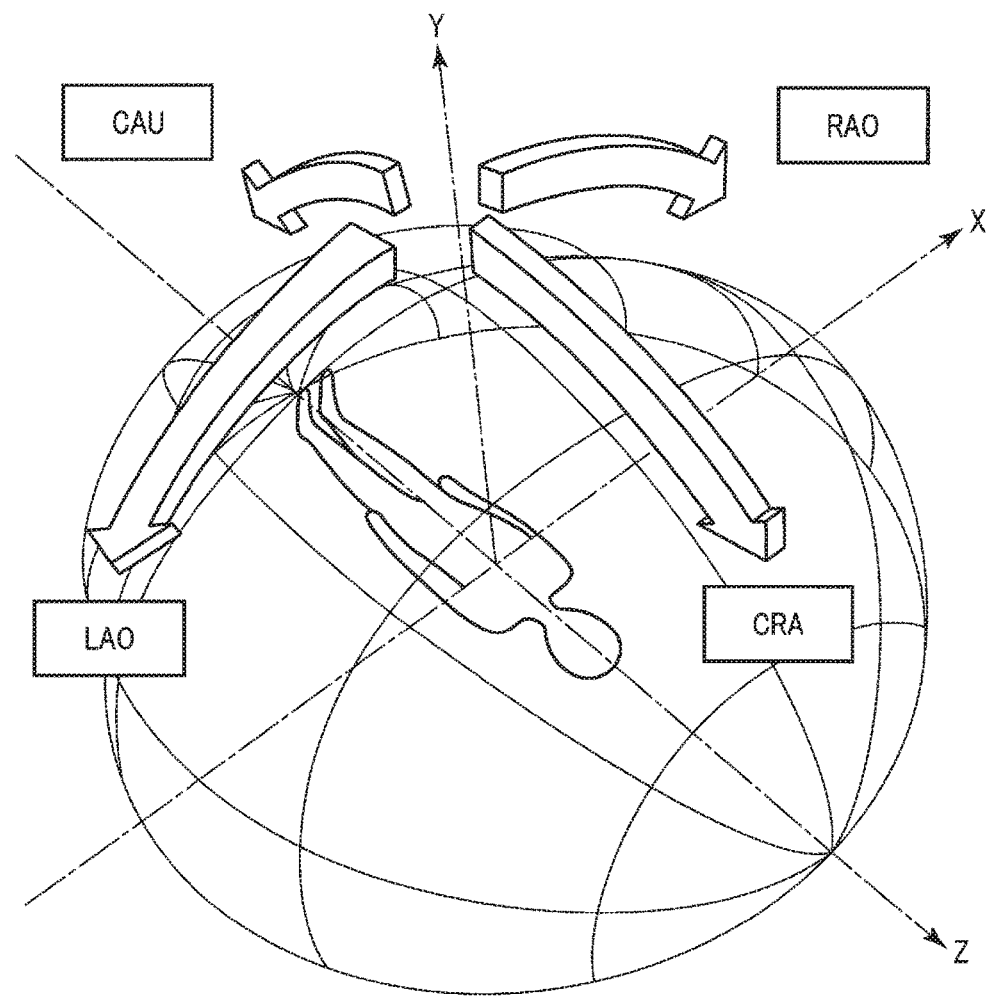
FIG. 4 is a view for explaining the movable ranges of a C-arm and Ω-arm.

FIG. 4 is a view for explaining the movable ranges of the C-arm 12F and the Ω-arm 12L.

Referring to FIG. 4, a patient lies on the top. Referring to FIG. 4, the coordinate system is a clinical coordinate system with an imaging central position O as an origin. In the clinical coordinate system, an axis parallel to the body axis of a patient is defined as the Z-axis, an axis parallel to the frontal direction of a patient is defined as the Y-axis, and an axis orthogonal to the Y- and Z-axes is defined as the X-axis. As shown in FIG. 4, with the Y-axis along the frontal direction of a patient as a starting point, a rotational angle to the right hand side of a patient is defined as the first oblique position (Right Anterior Oblique view: to be referred to as RAO hereinafter), and a rotational angle to the left hand side is defined as the second oblique position (Left Anterior Oblique view: to be referred to as LAO hereinafter). With the Y-axis as a starting point, a rotational angle to the head side of the object is defined as a cranial direction (CRAnial: to be referred to as CRA hereinafter), and a rotational angle to the foot side of the object is defined as a caudal direction (CAUdal: to be referred to as CAU hereinafter). For example, the imaging central position, the isocenter G1 of the C-arm 12F, and the isocenter G2 of the Ω-arm 12L coincide with each other. In this case, RAO30 represents an angle of 30° through which the imaging central position O of the object is tilted from the frontal direction to the right hand side of a patient.

In general, an object is imaged while the C-arm 12F is inserted from the head side of a patient and the Ω-arm 12L is inserted from the lateral side of a patient. In this case, the rotation of the C-arm 12F to RAO and LAO is implemented by the holder rotation of the C-arm 12F. In addition, the rotation of the C-arm 12F to CRA or CAU is implemented by the slide rotation of the C-arm 12F. The rotation of the Ω-arm 12L to CRA or CAU is implemented by the holder rotation of the Ω-arm holder 128. In addition, the rotation of the Ω-arm 12L to RAO or LAO is implemented by the slide rotation of the Ω-arm 12L. When, for example, imaging is to be performed by using the C-arm 12F and the Ω-arm 12L, the rotational movement range of the C-arm 12F is defined as RAO120/LAO120 and CRA50/CAU45. In addition, at the time of rotational imaging, the C-arm 12F can rotate, for example, at a maximum rate of 60 deg/s. The rotational movement range of the Ω-arm 12L is defined as RAO120/LAO0 or RAO0/LAO120. In addition, the rotational movement range of the Ω-arm 12L is defined as CRA45/CAU50. At the time of rotational imaging, the Ω-arm 12L can rotate, for example, at a maximum rate of 30 deg/s.

The data processing apparatus includes input circuitry 21, the imaging controller 23, a system controller 24, an A/D convertor 25, an image memory 26, filtering circuitry 27, affine transformation circuitry 28, an LUT 29, a storage 31, computing circuitry 37, and a display 36.

Input circuitry 21 functions as a user interface for allowing the user to input instruction information to the X-ray diagnostic apparatus 1. Input circuitry 21 includes, for example, input devices such as a mouse, a keyboard, a trackball, a touch panel, and switches. For example, input circuitry 21 includes a fluoroscopy switch, an activation switch for collision check, a collision check switch, a 3D imaging condition switch, and an X-ray trigger switch. The fluoroscopy switch is a switch for instructing the start and end of X-ray fluoroscopy. The activation switch for collision check is a switch for setting the ON/OFF state of the collision check at the time of the execution of 3D imaging. A collision check is an operation of checking in advance collision between a patient and X-ray apparatus, between units of X-ray apparatus, and between units of X-ray apparatus and equipments used for intervention or examination. When the activation switch for collision check is ON, a collision check is executed under the control of the imaging controller 23 in response to the pressing of the collision check switch. A collision check will be described in detail later. Note that the ON/OFF state of the collision check does not need to set by the activation switch for collision check. For example, 3D imaging programs may include an item for setting the ON/OFF state of the collision check. The user sets the ON/OFF state of the collision check as a part of 3D imaging conditions in 3D imaging programs. The 3D imaging condition switch is a switch for setting each of the two imaging systems to an adequate FOV (imaging field of view) and SID (the distance between the focal point of the X-ray tube and the X-ray detector) for 3D imaging. The collision check switch is a switch for moving each of the two imaging systems from a rotation end position to a rotation start position for 3D imaging at lower speed. The X-ray trigger switch is a switch for starting X-ray acquisition with rotational DSA imaging mode from an adequate start angles, and is also a switch for instructing the start of gantry rotation to each of the two imaging systems. Note that these switches may be mechanical switches or software switches displayed on the display 36. These switches may be provided in a plurality of places. For example, switches may be provided on an imaging apparatus in an examination room and a data processing apparatus in a control room.

Input circuitry 21 may include an accuracy level switch. In response to the pressing of the accuracy level switch, the imaging controller 23 changes state for expected accuracy level of 3D imaging from accurate mode to speed mode, or vice versa.

Instruction information includes an instruction to set X-ray fluoroscopy conditions, an instruction to set a 3D road map program, and the like.

X-ray fluoroscopy conditions include condition items such as a tube voltage, a tube current, and an irradiation time (pulse width). For example, the user can input X-ray fluoroscopy conditions by an operation on a fluoroscopy condition setting screen. More specifically, the fluoroscopy condition setting screen has a plurality of input boxes in correspondence with a plurality of items. For example, the user can input a tube voltage condition by inputting a numerical value in an input box corresponding to a tube voltage with the keyboard. Note that the user may input X-ray fluoroscopy conditions by other methods. For example, the user can input X-ray fluoroscopy conditions selected from a plurality of X-ray fluoroscopy conditions. Assume, in this case, that the storage 31 stores the data of a plurality of X-ray fluoroscopy conditions together with additional information such as patient information (patient's age, sex, physique, and the like) and examination information (imaging region, attending physician, imaging method, and the like). The fluoroscopy condition setting screen has a plurality of X-ray fluoroscopy conditions arranged together with pieces of additional information respectively corresponding to them. The user can input X-ray fluoroscopy conditions from the plurality of X-ray fluoroscopy conditions with reference to patient information and examination information.

3D road mapping is a series of processing from performing 3D imaging to displaying a superimposed image. 3D road mapping is executed during real-time X-ray fluoroscopy. 3D imaging includes imaging for obtaining a plurality of mask images concerning a patient and imaging for obtaining a plurality of contrast images. A plurality of mask images has different imaging angles. A plurality of mask images is acquired while the two imaging systems are rotated around a patient before the injection of a contrast medium. In addition, a plurality of contrast images has different imaging angles. A plurality of contrast images are acquired while the two imaging systems are rotated around a patient after the injection of a contrast medium in the same manner as obtaining the mask images. A 3D road map program therefore contains conditions concerning 3D imaging (to be referred to as 3D imaging conditions hereinafter).

At the time of 3D imaging, the first imaging system F and the second imaging system L each execute an imaging operation corresponding to 3D imaging conditions under the control of the imaging controller 23. The 3D imaging conditions include the following conditions. The 3D imaging conditions include 3D imaging conditions concerning the first imaging system F and 3D imaging conditions concerning the second imaging system L.

(1) SID (Source to Image Distance: the distance between the image receptor and the X-ray focal point)

(2) FOV (Field Of View: effective field of view)

(3) Imaging angle range (4) Imaging angle interval (5) Rotational speed (6): X-ray conditions (tube voltage, tube current, irradiation time, and the like)

The user can input 3D imaging conditions by an operation on the 3D imaging condition setting screen. More specifically, the 3D imaging condition setting screen has a plurality of input boxes respectively corresponding to a plurality of items contained in the 3D imaging conditions. For example, the user can input an imaging angle range the first imaging system F by inputting a numerical value in an corresponding input box with the keyboard.

Note that the user may input 3D imaging conditions by other methods. For example, the user can input 3D imaging conditions by selecting them from a plurality of 3D imaging conditions. In this case, the storage 31 needs to store the data of a plurality of 3D imaging conditions. Each of the plurality of 3D imaging conditions is stored together with additional information such as patient information (patient's age, sex, physique, and the like) and examination information (imaging region, attending physician, imaging method, and the like). The 3D imaging condition setting screen has a plurality of 3D imaging conditions arranged together with pieces of additional information respectively corresponding to them. The user can input 3D imaging conditions selected from the plurality of 3D imaging conditions with reference to patient information and examination information.

Note that input circuitry 21 may automatically input 3D imaging conditions. For example, 3D road mapping is executed during fluoroscopy in accordance with an operation of input circuitry 21 by a doctor or the like. Therefore, at the start of 3D imaging, patient information and examination information have already been registered on the X-ray diagnostic apparatus 1. Input circuitry 21 automatically inputs 3D imaging conditions based on the patient information and the examination information input to the X-ray diagnostic apparatus 1. More specifically, input circuitry 21 inputs 3D imaging conditions selected from the plurality of 3D imaging conditions stored in the storage 31 in accordance with the patient information and the examination information input to the X-ray diagnostic apparatus 1.

Imaging condition setting circuitry 22 sets the imaging angle ranges, the imaging angle intervals, and the rotational speeds which are input via input circuitry 21. The imaging angle ranges include the first imaging angle range corresponding to the first imaging system F and the second imaging angle range corresponding to the second imaging system L. The first and second imaging angle ranges set by imaging condition setting circuitry 22 will be described in detail later.

Imaging condition setting circuitry 22 sets the first and second imaging angle ranges on rotational orbits having the same rotation axis. The rotational orbit of the first imaging system F does not need to coincide with the rotational orbit of the second imaging system L. When the rotation axis of the first imaging system F almost coincides with that of the second imaging system L, the central positions of reconstruction area almost coincide each other. With this setting, reconstruction accuracy of 3D imaging using two imaging systems would be similar with that of 3D imaging using one imaging systems if those 3D imaging conditions are competitive.

Imaging condition setting circuitry 22 can set different imaging angle ranges and different rotational speeds in the first and second imaging systems. Imaging condition setting circuitry 22 may decide rotational speeds so that the time duration covering the first imaging angle range with the first imaging system matches the time duration covering the second imaging angle range with the second imaging system. In addition, imaging condition setting circuitry 22 may decide the ratio between the first imaging angle range and the second imaging angle range based on the rotational speed of the first imaging system F and the rotational speed of the second imaging system L. Imaging condition setting circuitry 22 may decide frame rate (time interval between acquisitions of adjacent frames so that two imaging angle intervals match together. Imaging condition setting circuitry 22 may also decide imaging angle intervals based on the exposure dose of a patient.

The imaging controller 23 controls each unit to execute an X-ray imaging operation.

More specifically, the imaging controller 23 controls the driving assembly, the high voltage generator, and the X-ray detector in accordance with set conditions so as to synchronously perform the movement of the C-arm 12F, the movement of the Ω-arm 12L, the generation of X-rays, and the detection of X-rays. For example, in response to the pressing of the X-ray trigger switch, the imaging controller 23 controls the first high voltage generator 15F and the second high voltage generator 15L in accordance with set X-ray imaging conditions. At this time, the imaging controller 23 controls the first X-ray detector 14F and the second X-ray detector 14L in synchronism with control on the first high voltage generator 15F and the second high voltage generator 15L. In addition, the imaging controller 23 controls the operations of the image memory 26, subtraction circuitry 30, reconstruction circuitry 33, three-dimensional image processing circuitry 34, image combining circuitry 35, and the like. This generates the first obtained image data (first projection data) corresponding to the first imaging system F and the second obtained image data (second projection data) corresponding to the second imaging system L.

(Explanation of Collision Check)

The imaging controller 23 executes collision check using the first imaging system F and the second imaging system L in response to the pressing of the collision check switch when the activation switch for collision check is ON. The first imaging system F and the second imaging system L perform following operations under the control of the imaging controller 23 during collision check.

First of all, the first imaging system F and the second imaging system L are slowly moved to a corresponding rotation end position. Thereafter, the first imaging system F and the second imaging system L are rotationally moved to a corresponding rotation start position (starting point). At this time, the first imaging system F and the second imaging system L are rotationally moved along orbits in actual 3D imaging. In addition, the first imaging system F and the second imaging system L are rotated at a rate of 20 deg/s, which is lower than the actual rotational speed. With these collision checks, the user can check whether the patient, the table 10, the first imaging system F, the second imaging system L, monitors and other equipments such as injector and so on interfere each other during 3D imaging In addition, for example, when the collision check switch is ON, the imaging controller 23 activates the X-ray trigger switch in the examination room and the X-ray trigger switch in the control room. Therefore, the user can instruct the start of the acquisition of mask images and contrast images with either the X-ray trigger switch in the examination room or the X-ray trigger switch in the control room. When the collision check switch is OFF, the imaging controller 23 inactivates the X-ray trigger switch in the control room. At this time, the user can instruct the start of the acquisition of mask images and contrast images only with the X-ray trigger switch in the examination room. When the collision check switch is OFF, since no collision check has been executed, potential collision between a patient and imaging apparatus, that between units of imaging apparatus, and between units of X-ray apparatus and equipments used for intervention or examination has not been checked. Inactivating the X-ray trigger switch in the control room makes it necessary for the user to check potential collision in the examination room within short distance to potential collision points. This makes it possible to ensure safety of a patient during rotational imaging and avoid any kinds of potential collision even in a case of no collision check.

According to the above description, the user selects the ON/OFF state of the collision check mode. However, the imaging controller 23 may automatically set this ON/OFF state depending on whether relatively safe rotational imaging is to be performed. Relatively safe rotational imaging corresponds to a case in which each rotation range of the two imaging systems is narrow, a case in which each rotational speed of the two imaging systems is low, a case in which each rotational orbit of the two imaging systems is spaced apart from an object, and a case in which each rotational orbit of the two imaging systems is completely same with previous 3D imaging done a short time ago. Therefore, the imaging controller 23 can set the ON/OFF state of the collision check based on the rotational speed, imaging angle range, each SID of the first imaging system F and the second imaging system L which are contained in 3D imaging conditions, and previous 3D imaging conditions done a short time ago.

For example, the imaging controller 23 sets the collision check mode OFF when each rotational speed of the first imaging system F and the second imaging system L is low (e.g., 30 deg/s or less).

In addition, the imaging controller 23 sets the collision check mode OFF when each imaging angle range of the first imaging system F and the second imaging system L is narrow (e.g., 60° or less).

Furthermore, the imaging controller 23 sets the collision check mode OFF in accordance with the positional relationship between a patient and the first imaging system and the relationship between a patient and the second imaging system. For example, the imaging controller 23 sets the collision check mode OFF when the each SID of the first imaging system F and the second imaging system L is much wider for a patient. In addition, the imaging controller 23 may set the ON/OFF state of the collision check mode in accordance with a combination of the above rotational speeds, imaging angle ranges, and SIDS. Furthermore, the imaging controller 23 may set the ON/OFF state of the collision check mode in accordance with 3D imaging conditions set in the past. More specifically, the imaging controller 23 determines the necessity of a collision check under the currently set 3D imaging conditions and previously set 3D imaging conditions, which were set within certain time frame.

With the above processing, the imaging controller 23 can automatically set the ON/OFF state of the collision check mode in accordance with set 3D imaging conditions. This can eliminate several procedures in a series of workflows using the X-ray diagnostic apparatus 1. It is therefore possible to shorten examination or treatment time.

(Explanation of 3D Imaging)

In response to the pressing of the switch-ray trigger switch, the first imaging system F and the second imaging system L acquire a plurality of mask images and a plurality of contrast images under the control of the imaging controller 23. At this time, the imaging controller 23 controls the rotating operation of the first imaging system F and the rotating operation of the second imaging system L so as to prevent collision between the first imaging system F and the second imaging system L. Characteristic operations of the first imaging system F and the second imaging system L at the time of 3D imaging will be described with reference to FIG. 5.

Figure 5:
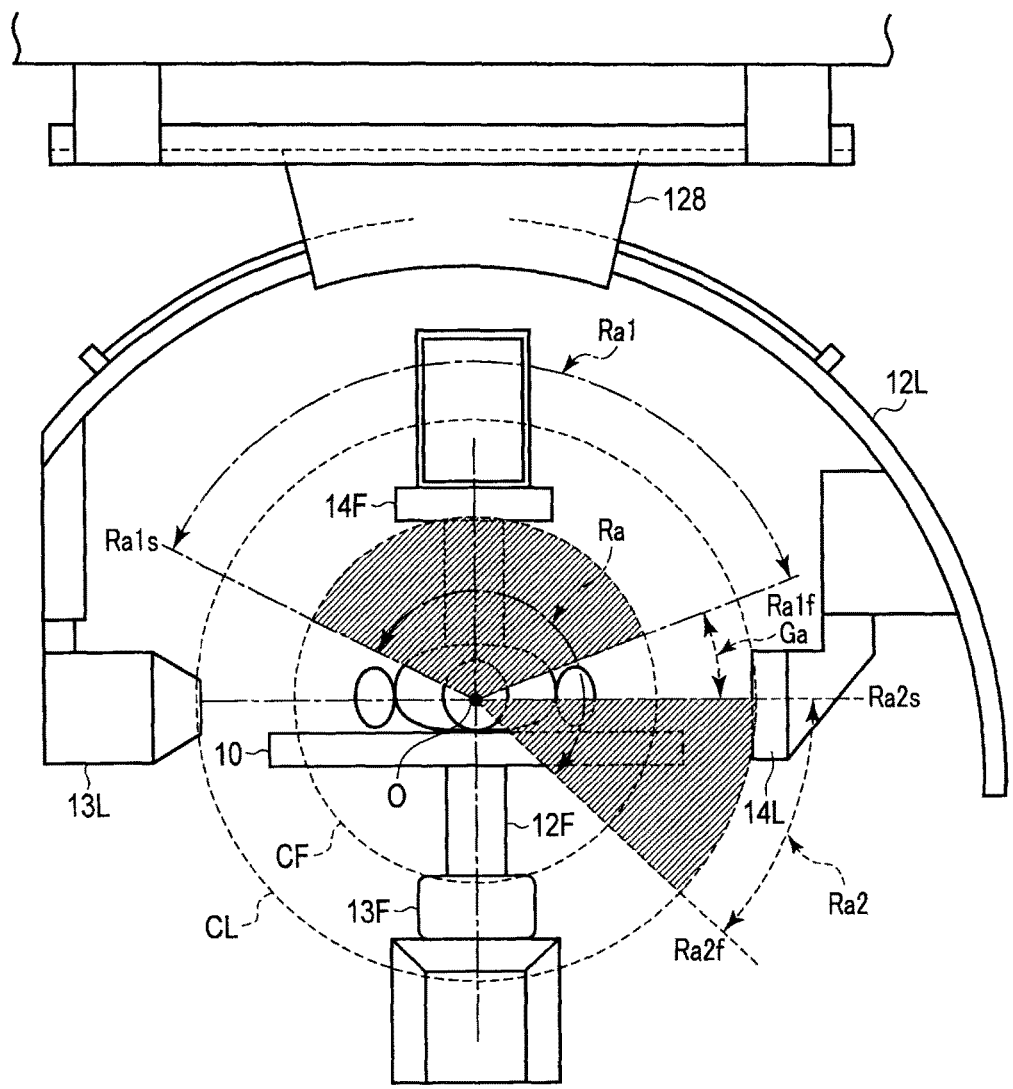
FIG. 5 is a view for explaining the imaging operations of the first and second imaging systems in 3D imaging.

FIG. 5 is a view for explaining the imaging operations of the first imaging system F and the second imaging system L in 3D imaging. The first imaging system F and the second imaging system L are aligned such that their isocenters O coincide with the central position of a target region. In addition, as shown in FIG. 5, a first imaging angle range Ra1 is set as the angle range in which the first imaging system F performs an imaging operation. Likewise, a second imaging angle range Ra2 is set as the angle range in which the second imaging system L performs an imaging operation. A deficiency angle (gap) Ga is provided between the first imaging angle range Ra1 and the second imaging angle range Ra2. That is, an imaging angle range in a projection data group (including a plurality of first projection data and a plurality of second projection data) has discontinuity. The deficiency angle is an angle in which no projection data is acquired. That is, when performing rotational imaging, focal spot of the first X-ray generator 13F and center of the first X-ray detector 14F of the first imaging system do not pass through the angle range corresponding to the deficiency angle, and focal spot of the second X-ray generator 13L and center of the second X-ray detector 14L of the second imaging system also do not pass through the angle range corresponding to the deficiency angle.

In this case, the angle range constituted by the first imaging angle range Ra1, the deficiency angle Ga, and the second imaging angle range Ra2 is defined as a target range Ra.

Before the pressing of the X-ray trigger switch, the first imaging system F is arranged at an imaging start position Ra1s in the first imaging angle range Ra1, and the second imaging system L is arranged at an imaging start position Ra2s in the second imaging angle range Ra2.

The imaging controller 23 executes a 3D imaging operation by using the first imaging system F and the second imaging system L in response to the pressing of the 3X-ray trigger switch. More specifically, the imaging controller 23 rotates the first imaging system F from the imaging start position Ra1s to an imaging end position Ra1f. During this rotation, the first imaging system F acquires a plurality of projection data corresponding to the first imaging angle range Ra1 in accordance with a set imaging angle interval. In addition, the imaging controller 23 rotates the second imaging system L from the imaging start position Ra2s to an imaging end position Ra1f. During this rotation, the second imaging system L acquires a plurality of projection data corresponding to the second imaging angle range Ra2 in accordance with a set imaging angle interval. At this time, the imaging controller 23 preferably controls the first imaging system F and the second imaging system L to make the first imaging system F and the second imaging system L simultaneously start rotating. In addition, as shown in FIG. 5, a rotational orbit CF of the first imaging system F and a rotational orbit CL of the second imaging system L have the same rotational center position. However, they may not be on the same circumference. Imaging condition setting circuitry 22 sets the first imaging angle range Ra1 and the second imaging angle range Ra2 so as to prevent the two imaging systems interfering each other when simultaneously rotating operations is ongoing. In addition, providing the deficiency angle Ga between the rotation ranges of the two imaging systems can reduce the risk of interference between the two imaging systems. For example, as shown in FIG. 5, if the deficiency angle Ga is provided to prevent interference between the first imaging system F arranged at the imaging end position Ra1f and the second imaging system L arranged at the imaging start position Ra2s, the two imaging systems do not interfere each other.

The X-ray diagnostic apparatus 1 described above can perform 3D imaging by using the two imaging systems. Therefore, there is no need to make one of the two imaging systems parks at parking position. This can shorten preparation time for 3D imaging.

The imaging controller 23 supplies an X-ray trigger to each first imaging system F and second imaging system L. In response to the reception of the X-ray trigger, each first imaging system F and second imaging system L executes X-ray imaging. At the time of 3D imaging, the imaging controller 23 repeatedly generates an X-ray trigger and supplies it to each first imaging system F and second imaging system L. Schemes of supplying X-ray triggers include a time trigger scheme and an angle trigger scheme. An imaging operation of the imaging controller 23 in the time trigger scheme will be described below with reference to FIG. 6.

Figure 6:
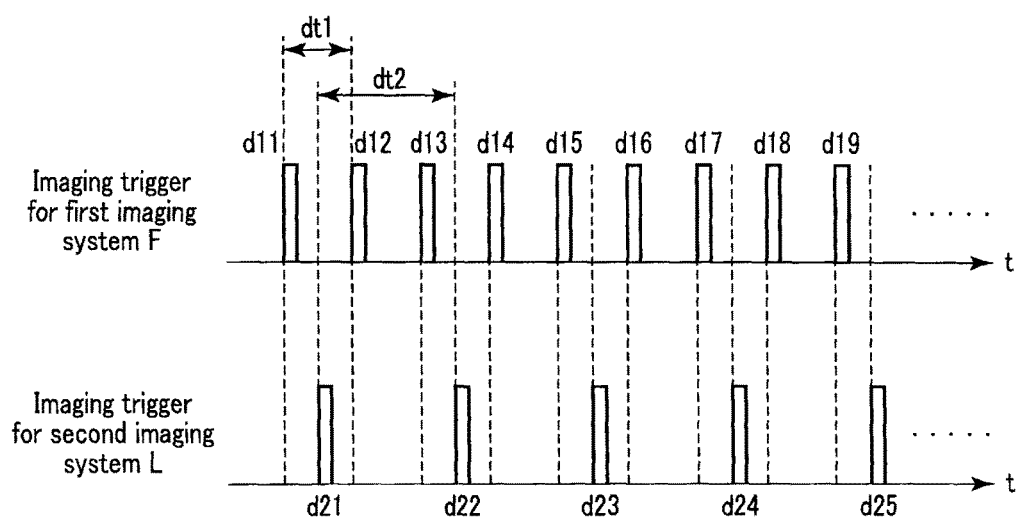
FIG. 6 is a graph showing an example of control on the first and second imaging systems by an imaging controller.

FIG. 6 is a view showing an example of control on the first imaging system F and the second imaging system L by the imaging controller 23. In the time trigger scheme, the imaging controller 23 repeatedly outputs an X-ray trigger to two imaging systems in accordance with the lapse of time. Two imaging systems performs an imaging operation in response to appearance of an X-ray trigger. Assume that the rotational speed of the first imaging system F is 60 deg/s, the rotational speed of the second imaging system L is 30 deg/s, and the imaging angle interval is 3°. In this case, the imaging angle interval of a plurality of first projection data and the imaging angle interval of a plurality of second projection data are set to 3° or less. In this case, as shown in FIG. 6, the imaging controller 23 generates X-ray triggers to set frame rate of the first imaging system F to 20 fps and to set frame rate of the second imaging system L to 10 fps. This allows each of the first imaging system F and the second imaging system L to acquire a plurality of projection images at imaging angle intervals of 3° on average. As shown in FIG. 6, X-ray triggers are generated to the first imaging system F at time intervals dt1, and X-ray triggers are generated to the second imaging system L at time intervals dt2. The time interval dt2 is twice as much as the time interval dt1. In the case of the time trigger scheme, imaging is performed in accordance with time intervals. In some cases, therefore, imaging cannot be performed at imaging angle intervals in an imaging angle range during the acceleration/deceleration of the rotating operation of each imaging system. In other words, in the case of the time trigger scheme, the rotational speed of each of the first imaging system F and the second imaging system L needs to be constant during an imaging operation. In some cases, each of the first imaging system F and the second imaging system L cannot rotate at a constant speed immediately after the start of a rotating operation. It is therefore necessary to set an approach-run range from an rotation start position to imaging start position, and to set a stop range from an imaging end position to rotation end position. An approach-run range and a stop range are set in advance. For example, each of them is set to about 5°. It is possible to change the approach-run range and the stop range, as needed, in accordance with user instructions. Note that imaging condition setting circuitry 22 may automatically set an approach-run range and a stop range in accordance with the rotational speed of two imaging systems.

Note that in the angle trigger scheme, there is no need to set any approach-run range or stop range. In the angle trigger scheme, the imaging controller 23 repeatedly outputs an X-ray trigger to two imaging systems in accordance with a rotational angle. Two imaging systems perform an imaging operation in response to appearance of an X-ray trigger. More specifically, the imaging controller 23 manages rotation angle of the first imaging system F and the second imaging system L, and specifies a rotation angle corresponding to each current rotational position of the first imaging system F and the second imaging system L. The imaging controller 23 then outputs an X-ray trigger when each rotational position of the first imaging system F and the second imaging system L matches to a preset rotation angle. This allows angle triggered acquisition at the first imaging system F and the second imaging system L.

The imaging controller 23 may also execute 3D imaging in the speed mode in response to the pressing of the accuracy level switch of input circuitry 21. The speed mode could eliminate preparation of an automatic contrast medium injector and collision check operation which spend certain time for 3D imaging. The imaging controller 23 performs a 3D imaging operation under 3D imaging conditions corresponding to the speed mode. Imaging condition setting circuitry 22 sets corresponding 3D imaging conditions which are stored in the storage 31. With this operation, the first imaging angle range and the second imaging angle range (to be described later) are set to a predetermined range (e.g., 60°) or less. In addition, each SID of the first imaging system F and the second imaging system L is set to a sufficient value. Note that in this case, imaging angle ranges and SIDs are set as 3D imaging conditions corresponding to the speed mode. In addition to them, however, the magnitude of a deficiency angle, the rotation speed of each imaging system, and the like may be set. When injecting a contrast medium by using a syringe instead of an automatic contrast medium injector, the injection time is about 3 s at most. For this reason, imaging condition setting circuitry 22 sets the first imaging angle range and the second imaging angle range such that it takes about 3 s or less for 3D imaging.

Since a 3D imaging operation can be executed under 3D imaging conditions which have less risk for incidents, a collision check can be omitted. This enables shorter preparation time for 3D imaging. In addition, the first imaging angle range and the second imaging angle range can be set shorter so that a syringe is used for injection of a contrast medium instead of an automatic contrast medium injector. This provides further shortening of the preparation time for 3D imaging.

The system controller 24 includes a CPU (Central Processing Unit) and a semiconductor memory. The system controller 24 temporarily stores, in the semiconductor memory, information input to the X-ray diagnostic apparatus via input circuitry 21. The system controller 24 comprehensively controls the respective units of the X-ray diagnostic apparatus based on the input information.

The A/D convertor 25 converts electrical signals to digital image data.

The image memory 26 stores the X-ray image data. This X-ray image data includes, for example, the first X-ray image data acquired at the first imaging system F, the second X-ray image data acquired at the second imaging system L.

Filtering circuitry 27 performs high-pass filtering or low-pass filtering for an X-ray image or the like. Affine transformation circuitry 28 performs enlargement, minification, rotation, movement and so on.

The LUT 29 performs tone conversion for an X-ray image or the like.

The storage 31 is, for example, a semiconductor storage device such as a Flash SSD (Solid State Disk) as a semiconductor storage element or an HDD (Hard Disk Drive). The storage 31 stores a plurality of DSA image data and 3D blood vessel image data. The storage 31 also stores the data of a plurality of 3D imaging conditions together with additional information such as patient information (patient's age, sex, physique, and the like) and examination information (imaging region, attending physician, imaging method, and the like). The additional information of 3D imaging conditions may include information concerning the ON/OFF state of the collision check mode (to be described later). In addition, the storage 31 stores 3D imaging condition data corresponding to the speed mode.

Computing circuitry 37 is implemented by, for example, a combination of a memory and a predetermined processor which implements programs. Note that this process may include one or a plurality of processors. Alternatively, the processor may be implemented by a processor shared by another arrangement. Computing circuitry 37 includes subtraction circuitry 30, image generation circuitry 32, reconstruction circuitry 33, three-dimensional image processing circuitry 34, and image combining circuitry 35.

Subtraction circuitry 30 generates DSA (DSA: Digital Subtraction Angiography) image data by performing subtraction processing of mask image data and corresponding contrast image data. Note that subtraction circuitry 30 may generate a subtraction image by subtracting a plurality of contrast image from calibration image (an image obtained in advance without any material which attenuates X-rays between X-ray focal spot and X-ray detector). Using a calibration image instead of using a mask image at subtraction step will reconstruct not only blood vessel information but also anatomical information but can obtain a road map image (to be described later) which allows the user to grasp the running of blood vessels. In addition, this technique obviates mask image acquisition, and hence can shorten total acquisition time, thereby enables shorter acquisition time and smaller exposure of a patient.

Image generation circuitry 32 generates an output signal from the first X-ray detector 14F and the second X-ray detector 14L. Generation process includes various types of correction processing, amplification processing, and A/D conversion processing. The pixel value assigned to each pixel constituting an X-ray image is, for example, a value corresponding to an X-ray attenuation coefficient concerning a material on the transmission path of X-rays.

Reconstruction circuitry 33 reconstructs volume data concerning blood vessels (to be referred to as 3D blood vessel image data hereinafter) from a plurality of DSA image data with different imaging angle ranges (a group of projection data including a plurality of first projection data and a plurality of second projection data).

As a reconstruction method, for example, a iterative reconstruction method is used. Equation (1) explains one of iterative reconstruction methods.

$$E = \|\vec{g} - H\vec{f}_e\|^2 + \alpha \|\vec{f}_e\|^2 \tag{1}$$

where g represents DSA image data arranged in column vectors on a pixel basis, fe represents reconstruction data to be obtained, and H is a projection matrix. Ideally, g is obtained by projecting fe with H. The iterative reconstruction method implements reconstruction by obtaining fe which minimizes E. The first term is a term for obtaining reconstruction data matching the acquired data. Even this term alone can obtain good reconstruction data fe with sufficient projection data. However, a plurality of DSA image data acquired by the X-ray diagnostic apparatus 1 does not cover sufficient angle range. That is, reconstruction circuitry 33 executes reconstruction processing based on insufficient information. For this reason, a reconstruction processing becomes unstable only with the first term, and reconstruct a 3D blood vessel image with much noise and artifacts. The second term has the effect of suppressing such noise and artifacts. For example, setting a to a large value will enhance the effect of suppressing noise and artifacts but degrade the sharpness of a 3D blood vessel image. On the other hand, setting a to a small value will reduce the effect of suppressing noise and artifacts but improve the sharpness of a 3D blood vessel image. The value of a is empirically decided from the information amount of obtained projection data. It is therefore preferable to prepare a plurality of presets concerning the value of a in advance. For example, four types of presets "Weak", "Mild", "Standard", and "Strong" are prepared in accordance with the magnitudes of the value of a. The user can obtain a 3D blood vessel image corresponding to a preset selected from the four types of presets. The user can further adjust the value of $\alpha$ referring an obtained 3D blood vessel image. For example, when smaller noise and artifacts are required, the user increases the value of $\alpha$. When the sharpness of an image is important, the user decreases the value of $\alpha$. Moreover, it is also possible to implement another iterative reconstruction algorithm such as ART (Algebraic Reconstruction Algorithm) method, EM (Expectation Maximization) method, or TV (Total Variation) method. Alternatively, it is possible to obtain a 3D blood vessel image from sufficient number of projection image and sufficient coverage of angular range by using a direct reconstruction method such as the Feldkamp method.

Three-dimensional image processing circuitry 34 generates road map image data showing vessel structures by executing three-dimensional image processing for 3D blood vessel image data stored in the storage 31. As three-dimensional image processing, for example, volume rendering with an optical system geometrically matching an X-ray projection system is used. In this case, a road map image is a rendering image. A rendering image is a two-dimensional image having undergone shading. Therefore, a road map image allows the user to grasp blood vessel structures three-dimensionally. Rendering is a kind of image processing for giving opacity, color, and shade to a two-dimensional image so as to stereoscopically express it. A view angle indicates a direction in which the user sees a 3D blood vessel image. A view angle is automatically determined in accordance with a change in the imaging angle of the C-arm 12F and a change in the imaging angle of the Ω-arm 12L. Note that the user may input a view angle via input circuitry 21. In addition, a road map image is not limited to a rendering image as long as it allows the user to grasp the running of blood vessels. For example, a road map image may be an image generated by performing image processing such as MIP (Maximum Intensity Projection) processing with the optical system, projection processing, or surface rendering processing for 3D blood vessel image data.

Image combining circuitry 35 generates the first superimposed image by superimposing a road map image on the first fluoroscopic image upon positional alignment. Image combining circuitry 35 generates the second superimposed image by superimposing a road map image on the second fluoroscopic image upon positional alignment.

The display 36 displays, on the monitor, the first and second superimposed images generated by image combining circuitry 35 in 3D road mapping. In general X-ray fluoroscopy, the display 36 displays the first and second fluoroscopic images on the monitor. Note that the display 36 may display superimposed images and fluoroscopic images while switching them in accordance with a user operation via input circuitry 21. Note that the number of monitors may increase. For example, it is possible to use four monitors display fluoroscopic images and superimposed images for the first imaging system F and the second imaging system L.

Imaging condition setting circuitry 22 sets the first imaging angle range and the second imaging angle range so as to set a target range to (180+α°) or less. In this case, a deficiency angle is provided between the first imaging angle range and the second imaging angle range. The angle α is decided based on the fan angles of the first imaging system F and the second imaging system L. For example, as the angle α, a larger fan angle of the first and second fan angles for the first imaging system F and the second imaging system L is used. A fan angle is the spread angle of an X-ray beam in the channel direction. Imaging condition setting circuitry 22 sets the first imaging angle range and the second imaging angle range in accordance with the conditions requested by the user. In other words, imaging condition setting circuitry 22 sets the magnitude of a deficiency angle and the position of the deficiency angle in a target range.

A method of setting a deficiency angle in a target range will be described first.

It is possible to shorten the acquisition time for 3D imaging by arranging a deficiency angle at a proper position in a target range. In addition, reduction of the acquisition time for 3D imaging can decrease the dose of contrast medium injected into a patient. At this time, imaging condition setting circuitry 22 sets the first imaging angle range and the second imaging angle range based on the rotational speeds of the two imaging systems. Assume that the rotational speed ratio between the first imaging system F and the second imaging system L is 2:1. In this case, imaging condition setting circuitry 22 sets the position of a deficiency angle such that the ratio between the first imaging angle range and the second imaging angle range becomes 2:1. Acquisition time at the first imaging system F and the second imaging system L is almost equivalent. For this reason, when performing 3D imaging by using the two imaging systems, contrast medium injected into a patient contribute for 3D imaging without any redundancy.

In addition, in order to suppress a deterioration of a 3D image quality, a deficiency angle is allocated at a proper position in a target range. When a 3D image is reconstructed from a plurality of projection data close to arbitrary rotational angle, artifacts appear along projection angle of those projection data. Therefore, it is possible to suppress the artifacts with projection data which project perpendicular to the previous projection angle. A pair of imaging directions which exhibit a high effect of suppressing artifacts a 3D image reconstruction in this manner will be referred to as an imaging direction set having an orthogonal relation. Note that the highest artifacts suppression effect is obtained in an imaging direction orthogonal to a given imaging direction. Even if, for example, an imaging direction is at 80° or the like with respect to the given imaging direction, the similar effect can be obtained.

As described above, imaging condition setting circuitry 22 sets the position of a deficiency angle based on artifacts suppression and shorter acquisition time.

Figure 7A:
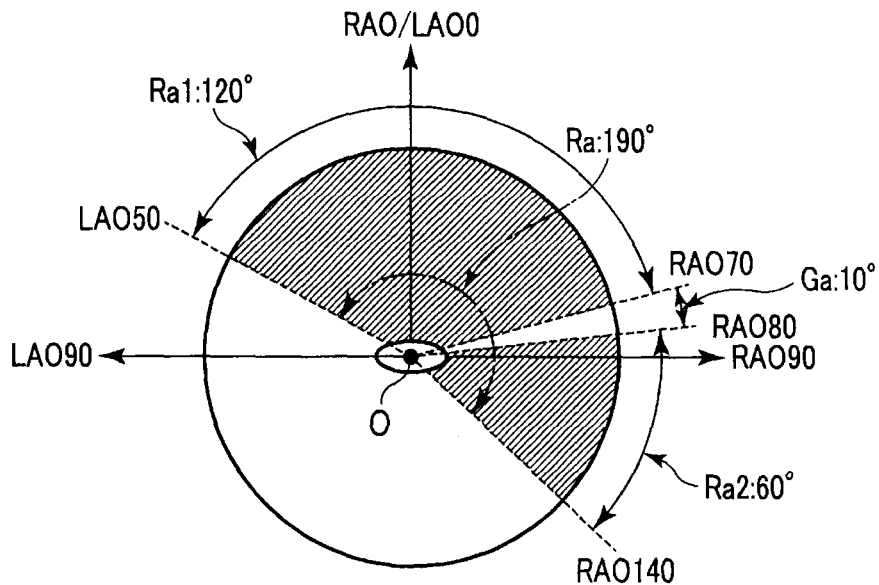
FIG. 7A is a view showing the first imaging angle range and the second imaging angle range set based on rotational speeds in the first example.
Figure 7B:
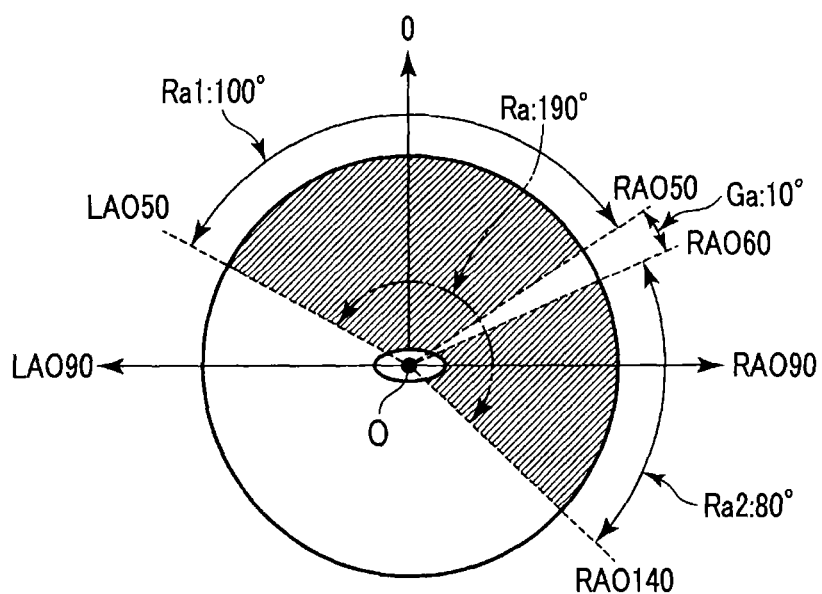
FIG. 7B is a view showing the first imaging angle range and the second imaging angle range which are set to increase the effect of suppressing the image quality deterioration of a 3D image in the first example.

FIGS. 7A and 7B are a view for explaining the first imaging angle range and the second imaging angle range set by imaging condition setting circuitry 22 in the first example in which a target range is (180+α°). For the sake of easy explanation, referring to FIGS. 7A and 7B, assume that the fan angle α is set to 10°, the target range Ra is set to 190° (from LAO50 to RAO140), and the deficiency angle Ga is set to 10°.

FIG. 7A is a view showing the first imaging angle range Ra1 and the second imaging angle range Ra2 set based on rotational speeds in the first example. Assume that the rotational speed of the first imaging system F is 60 deg/s, and the rotational speed of the second imaging system L is 30 deg/s. In this case, as shown in FIG. 7A, imaging condition setting circuitry 22 sets the first imaging angle range Ra1 to LAO50 to RAO70 and the second imaging angle range Ra2 to RAO80 to RAO140 so as to set the ratio between the first imaging angle range Ra1 and the second imaging angle range Ra2 to 2:1. The deficiency angle Ga is a angle from RAO70 to RAO80. With this setting, the first imaging angle range Ra1 is set to 120°, and the second imaging angle range Ra2 is set to 60°. This allows the second imaging system L to rotate in the second imaging angle range Ra2 in 2 s while the first imaging system F rotates in the first imaging angle range Ra1 in 2 s. Therefore, it is possible to shorten the acquisition time for 3D imaging by setting the first imaging angle range Ra1 and the second imaging angle range Ra2 as described in FIG. 7A.

In this case, according to the above description, the first imaging angle range Ra1 is set to LAO50 to RAO70, and the second imaging angle range Ra2 is set to RAO80 to RAO140. The first imaging angle range Ra1 and the second imaging angle range Ra2 are not allocated to satisfy the previous relationship. However, it does not matter when total angle of the first imaging angle range and the second imaging angle range is close to (180+α°). For example, the first imaging angle range Ra1 may be set to LAO70 to RAO50 (imaging angle range: 120°), and the second imaging angle range Ra2 may be set to RAO60 to RAO120 (imaging angle range: 60°). The angles at one end and the other end of the target range Ra are set in advance, and can be changed, as needed, in accordance with a user instruction. In many cases, however, the first imaging system F is normally arranged in the frontal direction (RAO)/LAO0), and the second imaging system L is normally arranged on the lateral side (RAO90 or LAO90). Therefore, the first imaging angle range Ra1 is preferably set between LAO90 and RAO90. In addition, when the second imaging angle range Ra2 is normally arranged at RAO90, the range is preferably set between RAO/LAO0 and RAO180.

FIG. 7B is a view showing the first imaging angle range Ra1 and the second imaging angle range Ra2 which are set to enhance the effect of suppressing a deterioration in the image quality of a 3D image in the first example. Imaging condition setting circuitry 22 sets the first imaging angle range Ra1 and the second imaging angle range Ra2 so as to include many imaging direction sets having orthogonal relations in the imaging angle range obtained by adding the first imaging angle range Ra1 to the second imaging angle range Ra2. As shown in FIG. 7B, imaging condition setting circuitry 22 sets the first imaging angle range Ra1 to LAO50 to RAO50, and the second imaging angle range Ra2 to RAO60 to RAO120. Therefore, the deficiency angle Ga is defined by RAO50 to RAO60. In this case, LAO50 to LAO40 of the first imaging angle range Ra1 have orthogonal relations with RAO40 to RAO50 of the first imaging angle range Ra1. In addition, LAO30 to RAO30 of the first imaging angle range Ra1 have orthogonal relations with RAO60 to RAO120 of the second imaging angle range Ra2. That is, the sum of angle ranges having orthogonal relations is 70°. It is therefore possible to suppress a deterioration in the 3D image quality by setting the first imaging angle range Ra1 and the second imaging angle range Ra2 as shown in FIG. 7B. Note that the first imaging angle range Ra1 and the second imaging angle range Ra2 may be set differently so as to achieve orthogonal relations.

As described above, imaging condition setting circuitry 22 can set the first imaging angle range and the second imaging angle range so as to satisfy purpose by thinking priority of acquisition time and 3D image quality. In addition, when shorter acquisition time is preferred, imaging condition setting circuitry 22 can set the first imaging angle range Ra1 and the second imaging angle range Ra2 to suppress a deterioration in the 3D image quality. Priority is given to one of the effects in accordance with a user instruction. Imaging condition setting circuitry 22 sets the first imaging angle range and the second imaging angle range in accordance with the priority order of the effects.

A method of setting the magnitude of a deficiency angle will be described next. In other words, setting the magnitude of a deficiency angle will set the sum of ranges in which the two imaging systems can perform imaging. Setting a large deficiency angle can shorten acquisition time. For this reason, increasing the deficiency angle will, for example, reduce the exposure dose and shorten the imaging time. In addition, shortening the imaging time can reduce the dose of contrast medium injected into a patient. In addition, increasing the deficiency angle can reduce the risk of interference between the two imaging systems. On the other hand, increasing the deficiency angle will increase reconstruction processing time to suppress reconstruction artifacts. A default value of a deficiency angle is set in advance to about 7°. However, it is possible to change a deficiency angle, as needed, in accordance with a user instruction. In this case, the user may directly input a deficiency angle, or a deficiency angle is determined from associated information. Associated information may include, for example, (1) an imaging time, (2) an exposure dose, (3) the dose of contrast medium, and (4) image quality (imaging condition).

(1) Imaging Time

Imaging condition setting circuitry 22 sets a deficiency angle in accordance with an input imaging time. Assume that the imaging time is "3 s". Assume that the rotational speed of the first imaging system F is 40 deg/s, and the rotational speed of the second imaging system L is 20 deg/s. In addition, for the sake of easy explanation, assume that fan angle α=20°. In this case, the range in which the first imaging system F can rotate in the designated time (3 s) is 120°, and the range in which the second imaging system L can rotate is 60°. Therefore, imaging condition setting circuitry 22 sets a deficiency angle to 20°.

In this manner, imaging condition setting circuitry 22 can set a deficiency angle in accordance with the imaging time designated by the user. When the user injects a contrast medium into a patient from a syringe instead of an automatic contrast medium injector, the injection time should be 3 s or less. In this case, imaging condition setting circuitry 22 can set the first imaging angle range and the second imaging angle range so as to set the imaging time to 3 s. Since the user can inject the contrast medium with the syringe, it is possible to shorten the preparation time for an automatic contrast medium injector, thereby total treatment time could be also shortened.

(2) Exposure Dose

Imaging condition setting circuitry 22 sets a deficiency angle in accordance with an input target value of an exposure dose. Let BmR be an expected exposure dose when 3D imaging is performed without any deficiency angle, and AmR be a target exposure dose requested by the user. In this case, the total angle of the two imaging systems is given by $(180+\alpha) \times A/B$. In this case, for the sake of easy explanation, assume that $A/B=4/5$ and $\alpha=20$. In this case, the total range of the two imaging systems is set to 160°, and a deficiency angle is set to 40°. Note that the reduction ratio of an exposure dose to an expected exposure dose may be input as associated information. For example, when the target exposure dose is expected to be half of the expected exposure dose, the user inputs "1/2".

Note that there are three potential methods to reduce an exposure dose. One is increasing a deficiency angle, second is decreasing total number of images by increasing imaging angle interval, and third is reducing X-ray conditions for each DSA image. The reduction in exposure dose described above is performed when it is necessary to further reduce the exposure dose upon execution of these measures.

(3) Dose of Contrast Medium

Imaging condition setting circuitry 22 sets a deficiency angle in accordance with an input dose of contrast medium. When, for example, the target blood vessel is the right or left vertebral artery, a contrast medium must be injected at an injection speed of 2 cc/s to obtain sufficient contrast. In addition, assume that it requires an inflow time of 0.5 s to enhance the contrast of a target blood vessel to some extent after the start of injection of the contrast medium. Information concerning a contrast medium injection speed and inflow time for each region is registered in advance in the X-ray diagnostic apparatus 1 in correspondence with each target blood vessel. Assume that the target region in 3D imaging is the left vertebral artery, and the dose of contrast medium injected is "6 cc". In this case, the contrast enhancement time is 3 s. Since the time required to enhance the contrast of the target blood vessel to some extent after the start of injection of the contrast medium into the object is 0.5 s, the imaging time is 2.5 s. Assume that the rotational speed of the first imaging system F is 40 deg/s, and the rotational speed of the second imaging system L is 20 deg/s, as in the above case. In addition, for the sake of easy explanation, assume that fan angle $\alpha=20°$. In this case, the angle range for which the first imaging system F can rotate is 100°, and the angle range for which the second imaging system L can rotate is 50°. Therefore, imaging condition setting circuitry 22 sets a deficiency angle to 50°.

(4) Image Quality (Imaging Condition)

Imaging condition setting circuitry 22 sets a deficiency angle in accordance with an input image quality. As information concerning an image quality to be input in this case, the user may selectively input from a plurality of indices corresponding to different deficiency angles to be set. In this case, a plurality of indices is image quality level. For example, those indices are "excellent", "good", "fair", "poor", and the like. Those indices corresponds to deficiency angles, for example, 0°, 10°, 20°, and 40°, respectively. The assignment of these deficiency angles is set in advance, and can be changed, as needed, in accordance with a user instruction. The complexities of blood vessels may be used as indices alternatively. For example, indices like "complex", "simple", and "average" are assigned to complex blood vessels like those in the head region, simple blood vessels in the neck region, and average blood vessels in the other region. The user may select an index in accordance with the complexity of target blood vessels.

Note that the user can input a plurality of types of associated information. In accordance with the plurality of types of associated information, imaging condition setting circuitry 22 specifies deficiency angles according to the associated information. Note that if an image quality is input, a priority level may be set for each piece of associated information so as to determine a deficiency angle based on the image quality.

The above method of setting the first imaging angle range Ra1 and the second imaging angle range Ra2 by imaging condition setting circuitry 22 can be used when the target range Ra is $(180+\alpha°)$. On the other hand, if the total range in which the two imaging systems can perform imaging is small, in other words, a deficiency angle to be set is large, the target range Ra may be less than $(180+\alpha°)$.

Imaging condition setting circuitry 22 sets the first imaging angle range such that the frontal direction (RAO/LAO0) is located in the center of the range. Likewise, imaging condition setting circuitry 22 sets the second imaging angle range such that the lateral direction (RAO90 or LAO90) is located in the center of the range.

Imaging condition setting circuitry 22 sets the first imaging angle range and the second imaging angle range in accordance with the ratio in rotational speed between the first imaging system F and the second imaging system L so as to shorten the acquisition time for 3D imaging. In this case, the ratio between the first imaging angle range and the second imaging angle range coincides with the ratio in rotational speed between the first imaging system F and the second imaging system L.

In addition, in order to suppress a deterioration in the 3D image quality, imaging condition setting circuitry 22 sets perpendicular relation between the first imaging angle range and the second imaging angle range as much as possible.

FIGS. 8A and 8B are a view for explaining the first imaging angle range and the second imaging angle range set by imaging condition setting circuitry 22 in the second example in which a target range is less than $(180+\alpha°)$. For the sake of easy explanation, referring to FIGS. 8A and 8B, assume that the fan angle $\alpha$ is 10°, the minimum deficiency angle is 10°, and the total angle in which imaging can be performed is 150°.

FIG. 8A is a view showing the first imaging angle range Ra1 and the second imaging angle range Ra2 set based on rotational speeds in the second example. Assume that the rotational speed of the first imaging system F is 60 deg/s, and the rotational speed of the second imaging system L is 30 deg/s. In this case, as shown in FIG. 8A, imaging condition setting circuitry 22 sets the first imaging angle range Ra1 to LAO50 to RAO50 and the second imaging angle range Ra2 to RAO65 to RAO115 so as to set the ratio between the first imaging angle range Ra1 and the second imaging angle range Ra2 to 2:1. With this setting, the first imaging angle range Ra1 is set to 100°, and the second imaging angle range Ra2 is set to 50°. In addition, the center of the first imaging angle range Ra1 is set to RAO/LAO0, and the center of the second imaging angle range Ra2 is set to RAO90. Furthermore, the deficiency angle between the first imaging angle range Ra1 and the second imaging angle range Ra2 is 15°, which is larger than the minimum deficiency angle. Setting the first imaging angle range Ra1 and the second imaging angle range Ra2 in the above manner can obtain the same effects as those described with reference to FIG. 7A. That is, it is possible to set the same acquisition time for the first imaging system F and the second imaging system L, thereby total acquisition time for 3D imaging could be shortened.

FIG. 8B is a view showing the first imaging angle range Ra1 and the second imaging angle range Ra2 which are set to suppress a deterioration in the 3D image quality in the second example. Imaging condition setting circuitry 22 sets the first imaging angle range Ra1 to LAO37.5 to RAO37.5, and the second imaging angle range Ra2 to RAO52.5 to RAO127.5 so as to set the first imaging angle range Ra1 and the second imaging angle range Ra2 to the same range. With this setting, the first imaging angle range Ra1 is set to 75°, and the second imaging angle range Ra2 is set to 75°. In addition, the center of the first imaging angle range Ra1 is set to RAO/LAO0, and the center of the second imaging angle range Ra2 is set to RAO90. In addition, the deficiency angle between the first imaging angle range Ra1 and the second imaging angle range Ra2 is 15°, which is larger than the minimum deficiency angle. Setting the first imaging angle range Ra1 and the second imaging angle range Ra2 in the above manner have an orthogonal relation, thereby the same effects as those described with reference to FIG. 7B could be obtained. That is, it is possible to suppress a deterioration in the 3D image quality.

As described above, imaging condition setting circuitry 22 can set the first imaging angle range Ra1 and the second imaging angle range Ra2 so as to get maximum benefits based on clinical requirements. Those benefits are one of image quality or shorter acquisition time. In addition, imaging condition setting circuitry 22 can set the first imaging angle range and the second imaging angle range to suppress a deterioration in the 3D image quality. Priority is decided according to clinical requirements with a user instruction. Imaging condition setting circuitry 22 sets the first imaging angle range and the second imaging angle range in accordance with the priority.

Note that the center of the first imaging angle range and the center of the second imaging angle range, which are set by the imaging condition setting circuitry 22, does not need to be the frontal direction (RAO/LAO) and the lateral direction (RAO90 or LAO90), respectively. But the center of the first imaging angle range and the center of the second imaging angle should have an orthogonal relation. Reference positions are often arranged in the frontal direction in the first imaging system F and in the lateral direction in the second imaging system L, respectively. Arranging the centers of the imaging angle ranges of the two imaging systems at the reference position scan reduce the risk of interference between a patient and the imaging systems. In addition, arranging the centers of the imaging angle ranges of the two imaging systems at or near those during immediately preceding fluoroscopy can save the time taken for the movement of the two imaging systems, thereby providing the effect of shortening the time in a series of workflows.

Referring to FIGS. 7A and 7B, the fan angle α is 10°, the target range Ra is 190°, and the deficiency angle Ga is 10°. Referring to FIGS. 8A and 8B, the fan angle α is 10°, the minimum deficiency angle is 10°, and the total angle in which imaging can be performed is 150°. However, this embodiment is not limited to them. For example, the total angle of the first imaging angle range and the second imaging angle range may be equal to or less than 165°, and the deficiency angle may be equal to or more than 7°.

A series of workflows using the X-ray diagnostic apparatus 1 will be described below with reference to FIG. 9.

Figure 9:
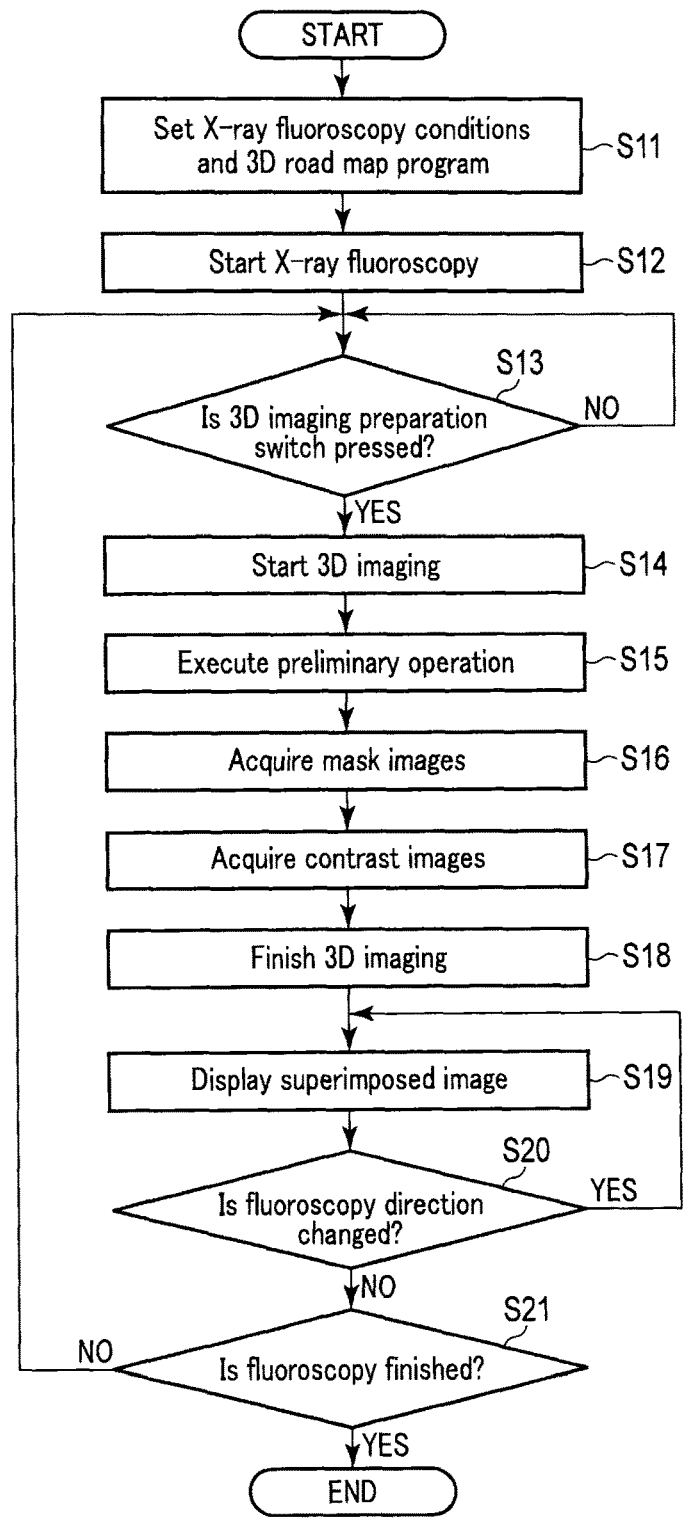
FIG. 9 is a flowchart showing a workflow procedure using an X-ray diagnostic apparatus.

FIG. 9 is a flowchart showing a workflow procedure using the X-ray diagnostic apparatus 1. The following will exemplify a case in which the preliminary operation mode is ON.

(Step S11): Setting of X-Ray Fluoroscopy Conditions and DSA Imaging Program

X-ray fluoroscopy conditions and the DSA imaging program are set via input circuitry 21. In this case, DSA imaging conditions are set.

(Step S12): Start of X-Ray Fluoroscopy

X-ray fluoroscopy is started in response to the pressing of the fluoroscopy switch. The display 36 displays the first fluoroscopic image corresponding to the first imaging system F and the second fluoroscopic image corresponding to the second imaging system L. The user performs operations such as inserting a guidewire or catheter into a patient while seeing the monitor.

(Step S13): Selection of 3D Imaging Program

When it becomes difficult to insert the guidewire or catheter into interested branch, the user selects the 3D imaging program. If the 3D imaging program is selected, the process shifts to step S14.

(Step S14): Patient Alignment

The X-ray diagnostic apparatus 1 shifts from X-ray fluoroscopy to preparation for 3D imaging. More specifically, the imaging controller 23 moves the first imaging system F and the second imaging system L so as to set SIDs and FOVs complying with the 3D imaging conditions. When the first imaging system F and the second imaging system L are set in accordance with the SIDs and the FOVs for 3D imaging, the user adjusts the position of a patient under X-ray fluoroscopy. The user may also adjust X-ray conditions while seeing the first fluoroscopic image and the second fluoroscopic image.

(Step S15): Collision Check

Upon completion of the adjustment of the position of a patient, the user presses the collision check switch. In response to the pressing of the collision check switch, the imaging controller 23 executes a collision check operation for the first imaging system F and the second imaging system L. First of all, the first imaging system F and the second imaging system L is moved to the rotation end position. Then the first imaging system F and the second imaging system L are slowly rotated and moved to the rotation start position along rotation orbits, and a collision check operation is finished. After the execution of the collision check operation, the first imaging system F and the second imaging system L are at the rotation start positions. At this stage, the user fills a contrast medium into a syringe and connects it to a catheter.

If, for example, the control scheme by which the imaging controller 23 controls the first imaging system F and the second imaging system L is the time trigger scheme, the rotation start position is the approach-run start position, and the rotation end position is the stop position. If the control scheme is the angle trigger scheme, the rotation start position is the imaging start position, and the rotation end position is the imaging end position.

Note that in the speed mode, step S15 can be omitted.

(Step S16): Acquisition of Mask Images

In response to the pressing of the X-ray trigger switch, the imaging controller 23 starts acquiring mask images. Upon completion of the acquisition of mask images, the imaging controller 23 returns the first imaging system F and the second imaging system L to the rotation start position. The image memory 26 stores the acquired mask image data, together with imaging angle data.

(Step S17): Acquisition of Contrast Images

When the first imaging system F and the second imaging system L return, the user injects contrast medium into a patient from the syringe. Keeping the X-ray trigger switch pressed will cause the imaging controller 23 to start acquiring contrast images after the lapse of a predetermined time. Upon completion of 3D imaging, each of the first imaging system F and the second imaging system L is automatically returned to a preset position. For example, the first imaging system F is moved to the frontal position of the patient, and the second imaging system L is moved to the lateral position of the patient. Note that the preset positions does not need to be the frontal position and lateral position of the patient. For example, each of the first imaging system F and the second imaging system L may be returned to the position stayed when the 3D imaging program is selected. Returning imaging system to the previous operation positions allows the user to continue an operation, thus reducing restoration time. In general, however, when the user performs an operation, the first X-ray detector 14F is often located near the second X-ray detector 14L. For this reason, upon completion of 3D imaging, each of the first imaging system F and the second imaging system L may be moved to a preset position in response to switch operation by the user or the like, instead of being automatically returned to a previous position. The image memory 26 stores the acquired contrast image data, together with imaging angle data.

(Step S18): 3D Reconstruction

Subtraction circuitry 30 generates a plurality of DSA image data based on a plurality of contrast images and a plurality of mask images whose imaging angles are almost same. Reconstruction circuitry 33 then reconstructs 3D blood vessel image data based on the plurality of DSA image data. With the processing from step S13 to step S18, 3D imaging is completed.

(Step S19): Display of Superimposed Image

Three-dimensional image processing circuitry 34 generates the first road map image corresponding to the fluoroscopy direction of the first imaging system F based on the 3D blood vessel image data. In addition, three-dimensional image processing circuitry 34 generates the second road map image corresponding to the fluoroscopy direction of the second imaging system L based on the 3D blood vessel image data. Image combining circuitry 35 generates the data of the first superimposed image by superimposing the first fluoroscopic image on the first road map image. Image combining circuitry 35 also generates the data of the second superimposed image by superimposing the second fluoroscopic image on the second road map image. The display 36 displays the first superimposed image and the second superimposed image on the monitor.

(Step S20): Change of Fluoroscopy Direction

Every time the imaging controller 23 changes the fluoroscopy direction of each of the first imaging system F and the second imaging system L, the processing in step S19 is repeatedly executed. With this processing, the display 36 displays a superimposed image following fluoroscopy directions.

(Step S21): End of Fluoroscopy

The processing from step S13 to step S20 is repeatedly executed until the end of fluoroscopy. For example, when a patient moves, the process returns to step S13. Note that determination of the necessity to perform 3D imaging again may be decided by the user. Or, when fluoroscopy position is out of 3D blood vessel image data after a change, the system controller 24 may display a message notifying the necessity of 3D imaging on the display 36. Alternatively, the system controller 24 may display a message notifying the necessity of 3D imaging on the display 36 upon detecting that the position of a human body depicted on an X-ray fluoroscopic image has greatly moved. The user can recognize the necessity to perform 3D imaging again by checking the message.

With the processing from step S11 to step S21, a series of workflows using the X-ray diagnostic apparatus 1 is finished.

According to the X-ray diagnostic apparatus 1 described above, the following effects can be obtained.

The X-ray diagnostic apparatus 1 can perform 3D imaging of a 3D road map by using the two imaging systems. This obviates the necessity of user operations of making one of the two imaging systems retreat and returning it to the previous position. Therefore, using the X-ray diagnostic apparatus 1 can shorten the time taken in a series of workflows including 3D road mapping.

3D imaging conditions are provided with a deficiency angle between the first imaging angle range, in which the first imaging system F rotates, and the second imaging angle range, in which the second imaging system L rotates. This can reduce the risk of collision between the first imaging system F and the second imaging system L. In addition, 3D imaging with a deficiency angle can reduce the sum of rotational angles of the first imaging system F and the second imaging system L as compared with 3D imaging without any deficiency angle. This provides the effect of shortening the imaging time. In addition, 3D imaging with a deficiency angle can reduce the total time of imaging as compared with 3D imaging without any deficiency angle. This provides the effect of reducing the exposure dose of a patient and reducing amount of contrast medium injected into a patient.

However, a plurality of projection data acquired by 3D imaging with a deficiency angle include no projection data corresponding to the deficiency angle. For this reason, the X-ray diagnostic apparatus 1 reconstructs 3D blood vessel image data based on a plurality of projection data with insufficient 3D information. A 3D blood vessel image reconstructed with a deficiency angle contains more artifacts (and noise) than a 3D blood vessel image reconstructed without any deficiency angle under the same reconstruction conditions. However, the X-ray diagnostic apparatus 1 can suppress noise and artifacts by arranging the first imaging angle range and the second imaging angle range. On the other hand, how much image quality the user requires for a 3D blood vessel image depends on the size of a target to be checked by the user, the complexity of a region, or the like. If, for example, a blood vessels to be checked by the user is small and complicated, minimizing a deficiency angle may be suggested for a 3D blood vessel image. On the other hand, if a blood vessels to be checked by the user is major vessels, even setting a large deficiency angle may be acceptable for a 3D blood vessel image. That is, if a 3D blood vessel image has minimum image quality desired by the user, a deficiency angle could be large in 3D imaging.

Figure 10A:
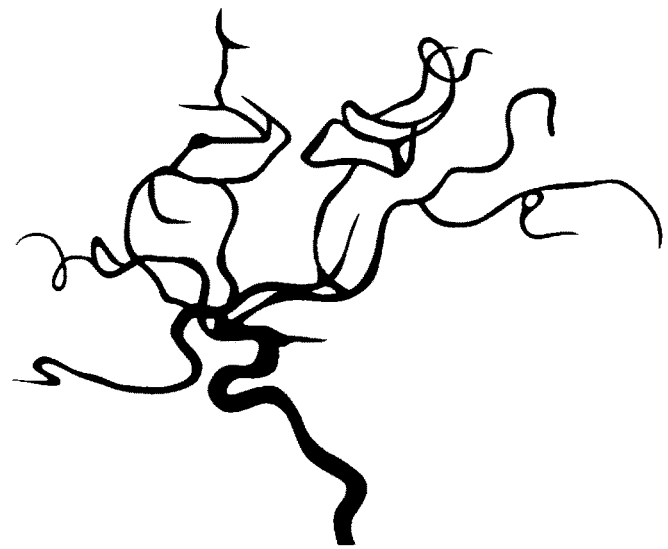
FIG. 10A is a view showing an example of a 3D road map obtained by an X-ray diagnostic apparatus according to this embodiment.
Figure 10B:
FIG. 10B is a view for explaining the effect obtained by this embodiment.

FIG. 10A is a view showing an example of a 3D road map obtained by the X-ray diagnostic apparatus according to this embodiment. FIG. 10B is a view for explaining the effect obtained by the embodiment. FIG. 10B shows an example of a 3D road map obtained by a conventional X-ray diagnostic apparatus.

A comparison between the 3D road map shown in FIG. 10A and the 3D road map shown in FIG. 10B indicates that the user cannot discriminate fine blood vessels shown in FIG. 10B by using the 3D road map shown in FIG. 10A. However, the 3D road map shown in FIG. 10A provides information precise enough to know the branching angle of a blood vessels as navigation purposes. If, for example, a blood vessels to be checked by the user is only major vessels, the user can discriminate the desired blood vessel on the 3D blood vessel image even with the 3D road map shown in FIG. 10A. This allows the user to obtain a 3D road map more quickly and easily than before. That is, the X-ray diagnostic apparatus according to this embodiment can obtain information precise enough to know the branching angle of a blood vessel as navigation purposes by providing a deficiency angle while, for example, shortening the time taken for 3D imaging, reducing the exposure dose, and decreasing the dose of contrast medium.

The X-ray diagnostic apparatus 1 can set the first imaging angle range, the second imaging angle range, and a deficiency angle in accordance with user requests. The a deficiency angle can be automatically or manually set in accordance with the acquisition time for 3D imaging, the total dose of contrast medium injected into a patient, and the exposure dose of the patient.

That is, providing a deficiency angle in a target range in 3D imaging produces the effects of, for example, shortening the time taken for 3D imaging, reducing the exposure dose, and decreasing the dose of contrast medium. On the other hand, a 3D blood vessel image obtained with a deficiency angle contains more noise and artifacts than a 3D blood vessel obtained without any deficiency angle. However, it is possible to reduce noise and artifacts on a 3D blood vessel image by two factors. One is alignment of projection directions of the first and second imaging systems, and second is appropriate reconstruction conditions. Image quality is adjusted to the extent that the user can check an operation (check) target. For this reason, the X-ray diagnostic apparatus 1 can reduce pain for a patient while maintaining the efficiency of the operation of the doctor in 3D road mapping.

In addition, the X-ray diagnostic apparatus 1 has the function of automatically returning the first imaging system F and the second imaging system L to preset positions or previous position after rotational imaging. This allows the user to return the first imaging system F and the second imaging system L to the positions immediately before 3D imaging, thereby the operation can restart with minimum time loss for 3D imaging.

Note that the effect of reducing an exposure dose by letting a target range include a deficiency angle in 3D imaging, which has been described in this embodiment, can also be applied to a single-plane X-ray diagnostic apparatus. That is, in the single-plane X-ray diagnostic apparatus, letting a target range in 3D imaging include a deficiency angle can reduce the number of times of imaging. This makes it possible to reduce the exposure dose of a patient. On the other hand, it is possible to suppress the occurrence of noise and artifacts on a 3D blood vessel image, which are caused when a target range in 3D imaging includes a deficiency angle, by adjusting image quality at 3D reconstruction. Image quality is adjusted to the extent that the user can check an operation (check) target. For this reason, the single-plane X-ray diagnostic apparatus can reduce pain for a patient while maintaining the efficiency of the operation by the doctor in 3D road mapping. However, unlike a biplane X-ray diagnostic apparatus, the single-plane X-ray diagnostic apparatus cannot properly adjust a deficiency angle (so as to make both the imaging angles become 90°). For this reason, the single-plane X-ray diagnostic apparatus needs to set a wider imaging angle than the biplane X-ray diagnostic apparatus in order to obtain image quality similar to that at the biplane X-ray diagnostic apparatus.

The words "predetermined processor" in the above description mean, for example, a dedicated or general-purpose processor, circuit (circuitry), processing circuit (circuitry), operation circuit (circuitry), or arithmetic circuit (circuitry), an ASIC (Application Specific Integrated Circuit), or a programmable logic device (e.g., an SPLD (Simple Programmable Logic Device), CPLD (Complex Programmable Logic Device), or FPGA (Field Programmable Gate Array)). In addition, each constituent element (each processing unit) of this embodiment may be implemented by a plurality of processors as well as a single processor. Furthermore, a plurality of constituent elements (a plurality of processing units) may be implemented by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus, comprising:
a first imaging system;
a second imaging system;
a first support member configured to support the first imaging system so as to allow the first imaging system to rotate about a first rotation axis;
a second support member configured to support the second imaging system so as to allow the second imaging system to rotate about a second rotation axis parallel to the first rotation axis;
control circuitry configured to
control the first imaging system and the first support member to acquire a plurality of first projection data only within a first imaging angle range while rotating the first imaging system from a first start angle to a first end angle, the first imaging angle range being a range from the first start angle to the first end angle, and
control the second imaging system and the second support member to acquire a plurality of second projection data only within a second imaging angle range while rotating the second imaging system from a second start angle to a second end angle, the second imaging angle range being a range from the second start angle to the second end angle, wherein a deficiency angle in which no projection data is acquired is present between the first end angle and the second start angle; and
reconstruction circuitry configured to reconstruct volume data from the plurality of first projection data and the plurality of second projection data,
wherein the control circuitry is further configured to set the deficiency angle based on at least one of an image quality index input by a user, an imaging time input by the user, an exposure dose input by the user, and a contrast medium dose input by the user.

2. The apparatus of claim 1, wherein a first X-ray tube and a first X-ray detector of the first imaging system, and a second X-ray tube and a second X-ray detector of the second imaging system do not pass through a range corresponding to the deficiency angle when performing rotational imaging.

3. The apparatus of claim 1, wherein a total angle of the first imaging angle range, the second imaging angle range, and the deficiency angle form a fan angle of 180° or less.

4. The apparatus of claim 1, wherein the first imaging angle range is larger than the second imaging angle range.

5. The apparatus of claim 1, wherein a central angle of the first imaging angle range is almost orthogonal to a central angle of the second imaging angle range.

6. The apparatus of claim 1, wherein the control circuitry is further configured to set the first imaging angle range and the second imaging angle range based on a ratio between a rotational speed of the first imaging system and a rotational speed of the second imaging system.

7. The apparatus of claim 1, wherein each of an imaging angle interval between the plurality of first projection data and an imaging angle interval between the plurality of second projection data is equal to 3° or more.

8. The apparatus of claim 1, wherein a rotational speed of the first imaging system is higher than a rotational speed of the second imaging system.

9. The apparatus of claim 1, wherein the control circuitry is further configured to decide at least one of a rotational speed of the first imaging system and a rotational speed of the second imaging system in accordance with a ratio between the first imaging angle range and the second imaging angle range.

10. The apparatus of claim 1, wherein the control circuitry is further configured to decide at least one of a rotational speed of the first imaging system and a rotational speed of the second imaging system so as to match an acquisition time for the plurality of first projection data by the first imaging system with an acquisition time for the plurality of second projection data by the second imaging system.

11. The apparatus of claim 1, further comprising input circuitry including a collision check selection switch configured to select an ON/OFF state of a collision check mode performed by the first imaging system and the second imaging system.

12. The apparatus of claim 11, wherein the control circuitry is further configured to validate an operation in the OFF state of the collision check mode when imaging conditions for the first imaging system, the first support member, the second imaging system, and the second support member are included in a predetermined condition range.

13. The apparatus of claim 12, wherein the control circuitry is further configured to validate an operation in the OFF state of the collision check mode in accordance with a one of rotational speed, imaging angle range and positional relationship between a patient and the first and second imaging system.

14. The apparatus of claim 11, wherein the input circuitry further includes, in each of an examination room and a control room, a X-ray trigger switch configured to trigger a start of acquisition of the plurality of first projection data by the first imaging system and trigger a start of acquisition of the plurality of second projection data by the second imaging system, and the control circuitry is further configured to, when the collision check mode is selected to OFF, activate an operation of the X-ray trigger switch in the examination room and inactivate an operation of the X-ray trigger switch in the control room when acquiring the plurality of first projection data by the first imaging system and acquiring the plurality of second projection data by the second imaging system.

15. The apparatus of claim 1, wherein the control circuitry is further configured to control the first support member and the second support member so as to move the first imaging system and the second imaging system to two predetermined or previous positions after acquisition of the plurality of first projection data and the plurality of second projection data.

16. The apparatus of claim 15, wherein the two predetermined positions include a frontal position of a patient and a lateral position of a patient.

17. The apparatus of claim 15, wherein the two predetermined positions include positions of the first and second imaging system when a 3D imaging program is selected.

18. The apparatus of claim 1, further comprising a display configured to display a 3D road map by displaying the reconstructed image on a fluoroscopic image obtained by at least one of the first imaging system and the second imaging system.

19. The apparatus of claim 1, wherein the control circuitry is configured to set the first imaging angle range, the second imaging angle range, and the deficiency angle prior to acquisition of the first and second projection data, and the reconstruction circuitry is configured to reconstruct the volume data only from the acquired first and second projection data.

* * * * *